US012150789B2

(12) United States Patent
Dickie

(10) Patent No.: US 12,150,789 B2
(45) Date of Patent: Nov. 26, 2024

(54) MACHINE LEARNING TECHNIQUES FOR MRI PROCESSING USING REGIONAL SCORING OF NON-PARAMETRIC VOXEL INTEGRITY RANKINGS

(71) Applicant: Optum, Inc., Minnetonka, MN (US)

(72) Inventor: David Alexander Dickie, Bishopton (GB)

(73) Assignee: Optum, Inc., Minnetonka, MN (US)

( * ) Notice: Subject to any disclaimer, the term of this patent is extended or adjusted under 35 U.S.C. 154(b) by 289 days.

(21) Appl. No.: 17/805,366

(22) Filed: Jun. 3, 2022

(65) Prior Publication Data

US 2023/0389879 A1  Dec. 7, 2023

(51) Int. Cl.
*A61B 5/00* (2006.01)
*A61B 5/055* (2006.01)
(Continued)

(52) U.S. Cl.
CPC .......... *A61B 5/7275* (2013.01); *A61B 5/0042* (2013.01); *A61B 5/055* (2013.01);
(Continued)

(58) Field of Classification Search
CPC .... A61B 6/468; A61B 5/1176; G06V 10/242; G06V 10/454; G06V 10/82; G06V 40/165;
(Continued)

(56) References Cited

U.S. PATENT DOCUMENTS 7,069,068 B1   6/2006  Ostergaard
8,364,254 B2   1/2013  Jacquin et al.
(Continued)

FOREIGN PATENT DOCUMENTS

EP   3471608 A1   4/2019
EP   3701495 A1   9/2020
(Continued)

OTHER PUBLICATIONS

Dickie, David Alexander et al. "The Brain Health Index: Towards a Combined Measure of Neurovascular and Neurodegenerative Structural Brain Injury," International Journal of Stroke, vol. 13, No. 8, pp. 849-856, Mar. 13, 2018, DOI: 10.1177/1747493018770222.
(Continued)

*Primary Examiner* — Edward F Urban
*Assistant Examiner* — Wassim Mahrouka
(74) *Attorney, Agent, or Firm* — ALSTON & BIRD LLP

(57) ABSTRACT

Various embodiments of the present invention provide methods, apparatus, systems, computing devices, computing entities, and/or the like for performing predictive recommendations using an MRI acquisition set associated with a common target object. Certain embodiments of the present invention utilize systems, methods, and computer program products that perform predictive recommendations based at least in part on an MRI set and utilizing one or more of techniques using image preprocessing models, techniques using image segmentation models, techniques using voxel integrity score generation machine learning models, and techniques using integrity score normalization models.

20 Claims, 11 Drawing Sheets

(51) Int. Cl.
   *G06T 7/00* (2017.01)
   *G06T 7/11* (2017.01)
   *G06V 10/762* (2022.01)

(52) U.S. Cl.
   CPC .............. *G06T 7/0012* (2013.01); *G06T 7/11* (2017.01); *G06V 10/762* (2022.01); *A61B 2576/026* (2013.01); *G06T 2200/04* (2013.01); *G06T 2207/10088* (2013.01); *G06T 2207/20081* (2013.01); *G06T 2207/30016* (2013.01); *G06V 2201/031* (2022.01)

(58) Field of Classification Search
   CPC .............. G06V 40/166; G06V 2201/07; G06V 2201/03; G06T 2207/10116; G06T 2207/20084; G06T 2207/30201; G06T 7/73
   See application file for complete search history.

(56) References Cited

U.S. PATENT DOCUMENTS

| | | |
|---|---|---|
| 2011/0144520 A1 | 6/2011 | Causevic et al. |
| 2017/0071470 A1* | 3/2017 | Cetingul .............. A61B 5/4064 |
| 2017/0188932 A1 | 7/2017 | Singer et al. |
| 2018/0268942 A1 | 9/2018 | Kamali-Zare et al. |
| 2019/0122363 A1* | 4/2019 | Greveson .............. A61B 6/032 |
| 2019/0164642 A1 | 5/2019 | Hartung et al. |
| 2019/0290130 A1 | 9/2019 | Zagorchev et al. |
| 2019/0392944 A1 | 12/2019 | Samset et al. |
| 2020/0143948 A1 | 5/2020 | Kamali-Zare et al. |
| 2021/0150671 A1 | 5/2021 | Guo et al. |
| 2021/0270848 A1 | 9/2021 | Mukaetova-Ladinska et al. |
| 2022/0189637 A1 | 6/2022 | Gurpur et al. |
| 2023/0238143 A1 | 7/2023 | Edmonds et al. |

FOREIGN PATENT DOCUMENTS

| | | |
|---|---|---|
| EP | 3863505 A1 | 8/2021 |
| KR | 10-2019-0015649 A | 2/2019 |
| KR | 2019-0015649 A | 2/2019 |
| WO | 2022/040137 A1 | 2/2022 |

OTHER PUBLICATIONS

Dickie, David Alexander et al. "Use of Brain MRI Atlases to Determine Boundaries of Age-Related Pathology: The Importance of Statistical Method," PLoS One, vol. 10, No. 5:e0127939, May 29, 2015, pp. 1-19, DOI: 10.1371/journal.pone.0127939.

Hasan, Ali M. et al. "Combining Deep and Handcrafted Image Features For MRI Brain Scan Classification," IEEE Access, vol. 7, Jun. 13, 2019, pp. 79959-79967, DOI: 10.1109/ACCESS.2019.2922691.

Sun, Xu et al. "Feature-Frequency-Adaptive On-Line Training For Fast and Accurate natural Language Processing," Association for Computational Linguistics, vol. 40, No. 3, pp. 563-586, Sep. 1, 2014, DOI: 10.1162/COLL_a_00193.

Danso, et al., "Developing an Explainable Machine Learning-Based Personalised Dementia Risk Prediction Model: A Transfer Learning Approach With Ensemble Learning Algorithms", Frontiers in Big Data, vol. 4, Article 613047, May 2021.

Department for Science, Innovation, and Technology, et al., "Sector Leaders to Drive Progress on National Dame Barbara Windsor Mission to Beat Dementia", UK Government Press Release, (8 pages), Mar. 20, 2023, https://www.gov.uk/government/news/sector-leaders-to-drive-progress-on-national-dame-barbara-windsor-mission-to-beat-dementia.

Extended European Search Report for European Patent Application No. 2218964.0, dated Sep. 26, 2023, (9 pages), European Patent Office, Munich, Germany.

\* cited by examiner

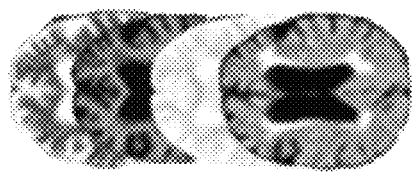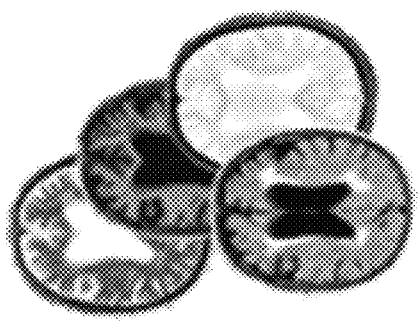
FIG. 5

_404_

```
┌─────────────────────────────────────────────────────┐
│ Generate a voxel integrity score for each image voxel associated
│ with the common target object
│ 601
└─────────────────────────────────────────────────────┘
                          │
                          ▼
┌─────────────────────────────────────────────────────┐
│ Generate a non-parametric integrity ranking for each image
│ voxel based at least in part on the voxel integrity score for the
│ image voxel
│ 602
└─────────────────────────────────────────────────────┘
                          │
                          ▼
┌─────────────────────────────────────────────────────┐
│ Generate the group of region scores based at least in part on each
│ non-parametric integrity ranking
│ 603
└─────────────────────────────────────────────────────┘
```

FIG. 6

| 904A-N | 906 | 907 |
|---|---|---|
| Disjoint Image Region | Predictive Recommendation Mapping Rules | Predictive Recommendation |
| Frontal and Temporal Lobes | (Average non-parametric integrity ranking) < 25th percentile | Investigation for Frontotemporal Dementia |
| Temporal Lobe and Hippocampus | (Ratio of Non-Threshold-Satisfying Non-Parametric Integrity Rankings and Threshold-Satisfying Non-Parametric Integrity Rankings) > 0.35 | Investigation for Alzheimer's type Dementia |
| Parietal and Occipital Lobes | (Ratio of Non-Threshold-Satisfying Non-Parametric Integrity Rankings and Threshold-Satisfying Non-Parametric Integrity Rankings) > 0.50 | Investigation for Posterior Cortical Atrophy (PCA) |
| Amygdala | (Average Non-Parametric Integrity Ranking) < 2.5th percentile | Investigation for Personality Disorder |
| Hippocampus and Periventricular White Matter | (Ratio of Non-Threshold-Satisfying Non-Parametric Integrity Rankings and Threshold-Satisfying Non-Parametric Integrity Rankings) > 0.25 | Investigation for Mixed Dementia |
| Periventricular White Matter | (Average Non-Parametric Integrity Ranking) < Median | Investigation for Vascular Dementia and Stroke Prevention Treatment |

Patient ID: 5235346436
MRI Analysis Results:

| Predicted Impact Region | Predictive Recommendation |
|---|---|
| Frontal and Temporal Lobes | Investigation for Frontotemporal Dementia |
| Amygdala | Investigation for Personality Disorder |

FIG. 10

MACHINE LEARNING TECHNIQUES FOR MRI PROCESSING USING REGIONAL SCORING OF NON-PARAMETRIC VOXEL INTEGRITY RANKINGS

BACKGROUND

Various embodiments of the present invention address technical challenges related to performing predictive recommendations using a magnetic resonance imaging (MRI) set and disclose innovative techniques for efficiently and effectively performing predictive recommendations using an MRI set.

BRIEF SUMMARY

In general, various embodiments of the present invention provide methods, apparatus, systems, computing devices, computing entities, and/or the like for performing predictive recommendations using a magnetic resonance imaging (MRI) set. Certain embodiments of the present invention utilize systems, methods, and computer program products that perform predictive recommendations using a magnetic resonance imaging (MRI) set by utilizing at least one of image preprocessing model, image segmentation model, voxel integrity score generation machine learning model, and integrity score normalization model.

In accordance with one aspect, a method is provided. In one embodiment, the method comprises: generating, using an image preprocessing model for the common target object type, and based at least in part on the MRI set, a standardized MRI set; generating, using an image segmentation model, and based at least in part on the standardized MRI set: (i) a plurality of disjoint image regions of the standardized MRI set, and (ii) for each disjoint image region, a subset of a group of image voxels of the standardized MRI set; for each image voxel: generating, using a voxel integrity score generation machine learning model, and based at least in part on a voxel input representation for the image voxel, a voxel integrity score for the image voxel, and generating, using an integrity score normalization model characterized by a normalization space that is defined by one or more normalization variables associated with the common target object, and based at least in part on the voxel integrity score for the image voxel, a non-parametric integrity ranking for the image voxel; generating a group of region scores based at least in part on each non-parametric integrity ranking, wherein: each region score is associated with a respective disjoint image region and is generated based at least in part on each non-parametric integrity ranking for those image voxels that are in the respective disjoint image region, and the group of region scores comprise, for each disjoint image region: (i) a normality-distribution region score that is generated based at least in part on an average measure of each non-parametric integrity ranking for those image voxels that are in the respective disjoint image region, and (ii) a normality-ratio region score that is generated based at least in part on a ratio of those image voxels that are in the disjoint image region and that are associated with non-threshold-satisfying non-parametric integrity rankings and those image voxels that are in the disjoint image region and that are associated with threshold-satisfying non-parametric integrity rankings, generating, using a predictive recommendation model and based at least in part on the group of region scores, the one or more predictive recommendations, wherein: the predictive recommendation model is configured to map the group of region scores to a selected subset of a plurality of candidate predictive recommendations; the predictive recommendation model is characterized by a plurality of predictive recommendation mapping rules comprising one or more normality-distribution predictive recommendation mapping rules and one or more normality-ratio predictive recommendation mapping rules, each normality-distribution predictive recommendation mapping rule is characterized by a normality-distribution region score threshold, and each normality-ratio predictive recommendation mapping rule is characterized by a normality-ratio region score threshold, and performing one or more prediction-based actions based at least in part on the selected subset.

In accordance with another aspect, a computer program product is provided. The computer program product may comprise at least one computer-readable storage medium having computer-readable program code portions stored therein, the computer-readable program code portions comprising executable portions configured to: generate, using an image preprocessing model for the common target object type, and based at least in part on the MRI set, a standardized MRI set; generate, using an image segmentation model, and based at least in part on the standardized MRI set: (i) a plurality of disjoint image regions of the standardized MRI set, and (ii) for each disjoint image region, a subset of a group of image voxels of the standardized MRI set; for each image voxel: generate, using a voxel integrity score generation machine learning model, and based at least in part on a voxel input representation for the image voxel, a voxel integrity score for the image voxel, and generate, using an integrity score normalization model characterized by a normalization space that is defined by one or more normalization variables associated with the common target object, and based at least in part on the voxel integrity score for the image voxel, a non-parametric integrity ranking for the image voxel; generate a group of region scores based at least in part on each non-parametric integrity ranking, wherein: each region score is associated with a respective disjoint image region and is generated based at least in part on each non-parametric integrity ranking for those image voxels that are in the respective disjoint image region, and the group of region scores comprise, for each disjoint image region: (i) a normality-distribution region score that is generated based at least in part on an average measure of each non-parametric integrity ranking for those image voxels that are in the respective disjoint image region, and (ii) a normality-ratio region score that is generated based at least in part on a ratio of those image voxels that are in the disjoint image region and that are associated with non-threshold-satisfying non-parametric integrity rankings and those image voxels that are in the disjoint image region and that are associated with threshold-satisfying non-parametric integrity rankings, generate, using a predictive recommendation model and based at least in part on the group of region scores, the one or more predictive recommendations, wherein: the predictive recommendation model is configured to map the group of region scores to a selected subset of a plurality of candidate predictive recommendations; the predictive recommendation model is characterized by a plurality of predictive recommendation mapping rules comprising one or more normality-distribution predictive recommendation mapping rules and one or more normality-ratio predictive recommendation mapping rules, each normality-distribution predictive recommendation mapping rule is characterized by a normality-distribution region score threshold, and each normality-ratio predictive recommendation mapping rule is characterized by a normality-ratio region score threshold, and perform one or more prediction-based actions based at least in part on the selected subset.

In accordance with yet another aspect, an apparatus comprising at least one processor and at least one memory including computer program code is provided. In one embodiment, the at least one memory and the computer program code may be configured to, with the processor, cause the apparatus to: generate, using an image preprocessing model for the common target object type, and based at least in part on the MRI set, a standardized MRI set; generate, using an image segmentation model, and based at least in part on the standardized MRI set: (i) a plurality of disjoint image regions of the standardized MRI set, and (ii) for each disjoint image region, a subset of a group of image voxels of the standardized MRI set; for each image voxel: generate, using a voxel integrity score generation machine learning model, and based at least in part on a voxel input representation for the image voxel, a voxel integrity score for the image voxel, and generate, using an integrity score normalization model characterized by a normalization space that is defined by one or more normalization variables associated with the common target object, and based at least in part on the voxel integrity score for the image voxel, a non-parametric integrity ranking for the image voxel; generate a group of region scores based at least in part on each non-parametric integrity ranking, wherein: each region score is associated with a respective disjoint image region and is generated based at least in part on each non-parametric integrity ranking for those image voxels that are in the respective disjoint image region, and the group of region scores comprise, for each disjoint image region: (i) a normality-distribution region score that is generated based at least in part on an average measure of each non-parametric integrity ranking for those image voxels that are in the respective disjoint image region, and (ii) a normality-ratio region score that is generated based at least in part on a ratio of those image voxels that are in the disjoint image region and that are associated with non-threshold-satisfying non-parametric integrity rankings and those image voxels that are in the disjoint image region and that are associated with threshold-satisfying non-parametric integrity rankings, generate, using a predictive recommendation model and based at least in part on the group of region scores, the one or more predictive recommendations, wherein: the predictive recommendation model is configured to map the group of region scores to a selected subset of a plurality of candidate predictive recommendations; the predictive recommendation model is characterized by a plurality of predictive recommendation mapping rules comprising one or more normality-distribution predictive recommendation mapping rules and one or more normality-ratio predictive recommendation mapping rules, each normality-distribution predictive recommendation mapping rule is characterized by a normality-distribution region score threshold, and each normality-ratio predictive recommendation mapping rule is characterized by a normality-ratio region score threshold, and perform one or more prediction-based actions based at least in part on the selected subset.

BRIEF DESCRIPTION OF THE SEVERAL VIEWS OF THE DRAWINGS

Reference will now be made to the accompanying drawings, which are not necessarily drawn to scale, and wherein:

FIG. 5 provides an operational example for a generating a standardized MRI set for a common target object in accordance with some embodiments discussed herein.

FIG. 6 provides a flowchart diagram of an example process for generating a group of region scores for a common target object. in accordance with some embodiments discussed herein.

FIGS. 9A-9B provide operational examples for predictive recommendation illustrating various predictive recommendation mapping rules in accordance with some embodiments discussed herein.

FIG. 10 provides an operational example of a prediction output user interface in accordance with some embodiments discussed herein.

DETAILED DESCRIPTION

Figure 1:
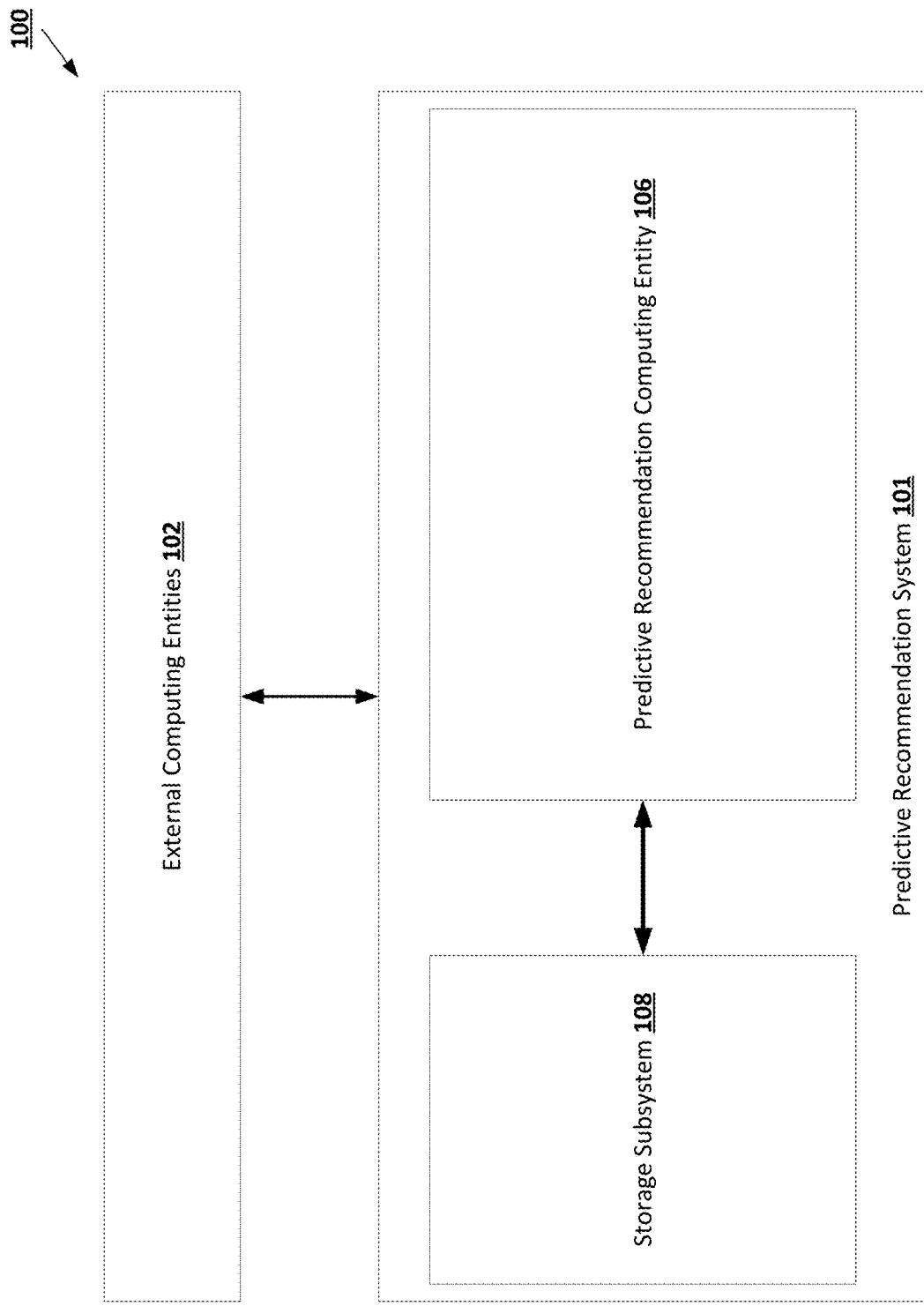
FIG. 1 provides an exemplary overview of an architecture that can be used to practice embodiments of the present invention.

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive recommendation with respect to an MRI set, one of ordinary skill in the art will recognize that the disclosed concepts can be used to perform other types of predictive recommendations.

I. Overview and Technical Advantages

Various embodiments of the present invention introduce techniques that improve the training speed of magnetic resonance imaging (MRI) set processing machine learning frameworks given a constant/target predictive accuracy by introducing a MRI set processing machine learning framework architecture that comprises an image preprocessing model, an image segmentation model, a voxel integrity score generation machine learning model, an integrity score normalization model, and a region scoring model. The combination of the noted components enables the proposed MRI set processing machine learning framework to generate more accurate MRI-based predictions, which in turn increases the training speed of the proposed MRI set processing machine learning framework given a constant predictive accuracy. It is well-understood in the relevant art that there is typically a tradeoff between predictive accuracy and training speed, such that it is trivial to improve training speed by reducing predictive accuracy, and thus the real challenge is to improve training speed without sacrificing predictive accuracy through innovative model architectures. See, e.g., Sun et al., *Feature-Frequency-Adaptive On-line Training for Fast and Accurate Natural Language Processing* in 40(3) Computational Linguistic 563 at Abst. ("Typically, we need to make a tradeoff between speed and accuracy. It is trivial to improve the training speed via sacrificing accuracy or to improve the accuracy via sacrificing speed. Nevertheless, it is nontrivial to improve the training speed and the accuracy at the same time"). Accordingly, techniques that improve predictive accuracy without harming training speed, such as various techniques described herein, enable improving training speed given a constant predictive accuracy. Therefore, by improving accuracy of performing MRI-based ML predictions, various embodiments of the present invention improve the training speed of magnetic resonance imaging (MRI) set processing machine learning frameworks given a constant/target predictive accuracy.

Various embodiments of the present invention make substantial technical improvements to performing operational load balancing for the post-prediction systems that perform post-prediction operations (e.g., automated specialist appointment scheduling operations) based on MRI-based predictions. For example, in some embodiments, a predictive recommendation computing entity determines D classifications for D MRI image sets based at least in part whether the selected region subset for each MRI image set as generated by the predictive recommendation model comprises a target region (e.g., a target brain region). Then, the count of D MRI image sets that are associated with an affirmative classification, along with a resource utilization ratio for each MRI image set, can be used to predict a predicted number of computing entities needed to perform post-prediction processing operations with respect to the D MRI image sets. For example, in some embodiments, the number of computing entities needed to perform post-prediction processing operations (e.g., automated specialist scheduling operations) with respect to D MRI image sets can be determined based at least in part on the output of the equation:

$$R = \text{ceil}\left(\sum_{k}^{k=K} ur_k\right),$$

where R is the predicted number of computing entities needed to perform post-prediction processing operations with respect to the D MRI image sets, ceil(.) is a ceiling function that returns the closest integer that is greater than or equal to the value provided as the input parameter of the ceiling function, k is an index variable that iterates over K MRI image sets among the D MRI image sets that are associated with affirmative classifications, and $ur_k$ is the estimated resource utilization ratio for a kth MRI image set that may be determined based at least in part on a patient history complexity of a patient associated with the MRI image set. In some embodiments, once R is generated, a predictive recommendation computing entity can use R to perform operational load balancing for a server system that is configured to perform post-prediction processing operations with respect to D MRI image sets. This may be done by allocating computing entities to the post-prediction processing operations if the number of currently-allocated computing entities is below R, and deallocating currently-allocated computing entities if the number of currently-allocated computing entities is above R.

Various embodiments of the present invention address technical challenges related to efficiently and effectively performing predictive recommendation using an MRI set of a common target object. The disclosed techniques improve the efficiency and effectiveness of performing predictive recommendations using an MRI set by utilizing a voxel integrity score generation machine learning model that is configured to generate a voxel integrity score based at least in part on voxel input representations of a standardized MRI set that is in turn is used to generate predictive inferences.

The voxel integrity score generation machine learning model utilizes operations that may, in at least some embodiments, reduce or eliminate the need for computationally expensive training operations in order to generate the noted voxel integrity score generation machine learning model. By reducing or eliminating the noted training operations, various embodiments of the present invention: (i) reduce or eliminate the computational operations needed for training and thus improves the computational efficiency of performing predictive recommendations using an MRI set, (ii) reduce or eliminate the need for storage resources to train/generate a voxel integrity score generation machine learning model and thus improve storage efficiency of performing predictive recommendations, and (iii) reduces or eliminates the need for transmitting extensive training data needed to generate voxel integrity score generation machine learning model and thus improves transmission/network efficiency of performing predictive recommendations using an MRI set. Via the noted advantages, various embodiments of the present invention make substantial technical contributions to the fields of predictive recommendations in particular and healthcare-related predictive recommendation in general.

An exemplary application of various embodiments of the present invention relates to generating predictive recommendations for a patient based at least in part on an MRI set of a brain region of the patient. Neurovascular and neurodegenerative diseases are characterized by progressive brain tissue loss and/or damage that is difficult to treat effectively once overtly expressed (e.g., via memory loss, diagnosis of dementia, or stroke). Signs of overt disease can be found in brain magnetic resonance imaging (MRI) scans more than ten (10) years prior to the onset of symptoms, which provides the potential for prognosis-based referral to specialist secondary services (e.g., cognitive impairment, Alzheimer's disease, and/or neurovascular clinics). These referrals would provide the opportunity for earlier treatment that may lead to better outcomes.

II. Definitions of Certain Terms

The term "common target object" may refer to a data object that is configured to describe a real-world entity and/or a virtual entity with respect to which one or more predictive recommendation operations are performed in order to generate one or more predictive recommendations. An example of a common target object may be a brain region (e.g., of a patient). In some embodiments a common target object (e.g., a brain region common target object) is associated with an MRI set of the common target object, where the MRI set comprises one or more MRI images of the common target object, and where the MRI set is processed in order to generate one or more predictive inferences (e.g., normality-ratio region scores and/or normality-distribution region scores) for the common target object, which in turn, may be used to generate predictive recommendations with respect to the common target object.

In some embodiments, a predictive recommendation may be a referral (e.g., medical referral) of a plurality of candidate referrals determined based at least in part on the one or more normality-ratio region scores and/or one or more normality-distribution region scores for the common target object. For example, the MRI set for a common target object that is a brain region common target object may be used to generate one or more normality-ratio region scores and/or one or more normality-distribution region scores for the brain region common target object, that in turn, may be used to generate predictive recommendations with respect to the common target object, where one or more of the predictive recommendations may be predictive recommendations with respect to a neurological condition, neurodegenerative condition, and/or neurovascular condition. In the noted example, a predictive recommendation may be a medical referral of a plurality of candidate medical referrals determined based at least in part on the one or more normality-ratio region scores and/or the one or more normality-distribution region scores associated with the brain region common target object, where the referral may be with respect to a monitored individual associated with the brain region common target object (e.g., brain region of the monitored individual). In various embodiments, the common target object is characterized by a plurality of disjoint regions that each correspond to a disjoint image region of a plurality of disjoint image regions of the MRI set associated with the common target object. In some embodiments, a common target object is associated with a common target object type, where each common target object associated with the common target object type may have one or more similar features/attributes. For example, a common target object that is a brain region common target object may be associated with a human brain region common target object type having similar features/attributes.

The term "magnetic resonance imaging (MRI) set" may refer to a data object that describes one or more MRI images (e.g., MRI image scan) of a common target object (e.g., a brain region), where each MRI image corresponds to an MRI image type of a plurality of MRI image types that are generated in accordance with a multi-sequence MRI acquisition protocol. A multi-sequence MRI acquisition protocol may describe instructions given to an MRI machine to generate various MRI image types, where each instruction/sequence results in generation of a particular MRI image type. Examples of MRI image types include a T1-weighted MRI image type, a T2-weighted MRI image type, a T2*-weighted MRI image type, and a Fluid Attenuated Inversion Recovery (FLAIR) MRI image type. In some embodiments, a particular MRI set may comprise a T1-weighted MRI image, a T2-weighted MRI image, a T2*-weighted MRI image, and a Fluid Attenuated Inversion Recovery (FLAIR) MRI image. In some embodiments, a common target object may be associated with a predictive entity, where a predictive entity may describe a real-world entity and/or virtual entity. For example, a predictive entity may describe a patient/individual. Accordingly, in some embodiments, a common target object may be associated with a patient/individual (e.g., a common target object may be the brain region of a patient/individual).

The term "standardized magnetic resonance imaging (MRI) set" may refer to a data object that describes an MRI set that has been preprocessed and configured to be utilized to generate predictive inferences (e.g., normality-ratio region scores and/or normality-distribution region scores) for a common target object associated with the standardized MRI set, where, as discussed above, the one or more predictive inferences may be utilized to determine one or more predictive recommendations with respect to the common target object. In some embodiments, the standardized MRI set may be preprocessed utilizing an image preprocessing model that is configured to perform one or more preprocessing operations with respect to each MRI image associated with the MRI set, and generate a standardized MRI set. In some embodiments the one or more preprocessing operations may comprise overlaying the MRI images associated with the MRI set on top of one another. Additionally, in some embodiments, the one or more preprocessing operations may comprise, for each MRI image of the MRI set, extracting a portion of the MRI image from the corresponding respective MRI image. For example, for a common target object that is a brain region common target object, for each respective MRI image, the portion of the MRI image corresponding to the brain may be extracted by, for example, removing the skull and other extra cranial structures from the MRI image.

In some embodiments, the standardized MRI set may be processed (e.g., utilizing an image segmentation model) to generate a plurality of disjoint image regions of the standardized MRI set, and a group of image voxels of the standardized MRI set, where each disjoint image region is associated with a subset of the group of image voxels of the standardized MRI set, and where each image voxel may be processed (e.g., using a voxel integrity score generation machine learning model) to generate a voxel integrity score for the respective image voxel. For example, the MRI set of a common target object may be defined by (or otherwise correspond to) a group of image voxels, where subsets of the group of image voxels correspond to various defined regions of the common target object. For example, in some embodiments, the common target object may be a brain region having defined regions (e.g., frontal lobes, temporal lobes, hippocampus, and the like). In the noted example, each defined region (e.g., frontal lobes, temporal lobes, hippocampus, and the like) may correspond to a subset of image voxels of the standardized MRI set of the brain region.

The term "image preprocessing model" may refer to a computer-implemented process configured to process an MRI set associated with a common target object in order to generate a standardized MRI set. Examples of image preprocessing model routines are described below. However, a person of ordinary skill in the art will recognize that other techniques may be utilized to generate a standardized MRI set. For example, an image preprocessing model may co-register/overlay the one or more MRI images associated with the MRI set in order to generate a standardized MRI set. As another example, for each MRI image of the MRI set, the image preprocessing model may extract a portion of the MRI image (e.g., brain) from the respective MRI image. In some embodiments the image preprocessing model may be a machine learning model.

The term "image segmentation model" may refer to a computer-implemented process configured to process a standardized MRI set associated with a common target object in order to generate a plurality of disjoint image regions of the standardized MRI set. Furthermore in some embodiments, the image segmentation model may be configured to process each disjoint image region of the plurality of disjoint image regions in order to generate a subset of image voxels of the group of image voxels of the standardized MRI set for each disjoint image region of the plurality of disjoint image regions. In some embodiments, the image segmentation model may be a machine learning model.

The term "voxel integrity score generation machine learning model" may refer to a data object that describes parameters, hyperparameters, and/or defined operations of a machine learning model that is configured to process voxel input representation of each image voxel of each disjoint image region of the standardized MRI set in order to generate a voxel integrity score for the respective image voxel, where for each disjoint image region, each voxel integrity score may be utilized to generate a non-parametric integrity ranking, which may in turn be utilized to generate one or more region scores (e.g., a normality-ratio region score and/or normality-distribution region score) for the disjoint image region. In some embodiments, the voxel integrity score generation machine learning model is a supervised machine learning model (e.g., neural network model) trained using label data, where the supervised machine learning model is configured to generate a voxel integrity score for each image voxel. In some embodiments, the voxel integrity score generation machine learning model is an unsupervised machine learning model (e.g., a clustering model). In some embodiments, the voxel integrity score generation machine learning model utilizes one or more clustering techniques. Examples of clustering techniques that may be used by the voxel integrity score generation machine learning model includes clustering techniques based at least in part on connectivity models (e.g., hierarchical clustering), based at least in part on centroid models (e.g., k-means algorithm), based at least in part on distribution models (e.g., using multivariate normal distributions), based at least in part on density models, and based at least in part on subspace model (e.g., using bi-clustering). An example of a voxel integrity score machine learning model is a gaussian mixture model cluster analysis machine learning model that is configured to process the image voxel for each disjoint image region in order to generate a non-parametric integrity ranking for the respective image voxel. In some embodiments, inputs to a voxel integrity score machine learning model include a vector or a matrix. In some embodiments, the outputs of a voxel integrity score machine learning model may include a non-parametric integrity ranking.

The term "integrity score normalization model" may refer to a computer-implemented process configured to process a voxel integrity score for an image voxel in order to generate a non-parametric integrity ranking for the image voxel. For example, in some embodiments the integrity score normalization model is configured to process each voxel integrity score for each image voxel of each disjoint image region of the MRI set in order to generate a non-parametric integrity ranking for each image voxel, that in turn, may be utilized to generate a group of region scores comprising a plurality of normality-distribution region scores and/or a plurality of normality-ratio region scores, where each disjoint image region of the MRI set is associated with a normality-distribution region score and/or a normality-ratio region score of the plurality of normality-distribution region scores and/or the plurality of normality-ratio region scores.

The term "voxel integrity score" may refer to a data object that is configured to describe a value that in turn describes the measure of a feature of a common target object with respect to a particular image voxel of an MRI set associated with the common target object. In some embodiments, the feature may be tissue integrity, where a voxel integrity score describes a tissue integrity measure with respect to a given image voxel of an MRI set. For example, in some embodiments, the voxel integrity score for an image voxel of an MRI set associated with a common target object that is a brain region may describe a value that describes a brain tissue integrity measure (e.g., brain tissue in the image voxel) for the particular image voxel of the MRI set. In some embodiments, the voxel integrity score is defined by a range of zero (0) to one (1), where values closer to one indicate a higher tissue integrity and values closer to zero indicate a lower tissue integrity. In various embodiments, a voxel integrity score may be generated for each image voxel of an MRI set of a common target object.

The term "threshold-satisfying non-parametric integrity ranking" may refer to a data entity that is configured to describe a non-parametric integrity ranking with respect to an image voxel that satisfies a defined integrity ranking threshold, where in some embodiments, a non-parametric integrity ranking that satisfies the defined integrity ranking threshold may be deemed to be associated with a normal classification (e.g., classified as normal). In some embodiments, for each disjoint image region of a common target object, each image voxel in the corresponding disjoint image region may be compared to the defined integrity ranking threshold in order to determine whether the respective image voxel is associated with a threshold-satisfying non-parametric integrity ranking or a non-threshold-satisfying non-parametric integrity ranking. For example, a non-parametric integrity ranking above the defined integrity ranking threshold may be deemed a threshold-satisfying non-parametric integrity ranking.

The term "non-threshold-satisfying non-parametric integrity ranking may refer to a data entity that is configured to describe a non-parametric integrity ranking with respect to an image voxel that fails to satisfy a defined integrity ranking threshold, where in some embodiments, a non-parametric integrity ranking that fails to satisfy the defined integrity ranking threshold may be deemed to be associated with an abnormal classification (e.g., classified as abnormal). In some embodiments, for each disjoint image region of a common target object, each image voxel in the corresponding disjoint image region may be compared to the defined integrity ranking threshold in order to determine whether the respective image voxel is associated with a threshold-satisfying non-parametric integrity ranking or a non-threshold-satisfying non-parametric integrity ranking. For example, a non-parametric integrity ranking below the defined integrity ranking threshold may be deemed a non-threshold-satisfying non-parametric integrity ranking.

III. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query, or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established, or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DINIM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 is a schematic diagram of an example architecture 100 for performing health-related predictive recommendations. The architecture 100 includes a predictive recommendation system 101 configured to receive health-related predictive recommendation requests from external computing entities 102, process the predictive recommendation requests to generate health-related predictive recommendations, provide the generated health-related predictive recommendations to the external computing entities 102, and automatically perform prediction-based actions based at least in part on the generated predictive recommendations. Examples of health-related predictive recommendations include health-related referrals (e.g., dementia investigation referral, posterior atrophy investigation referral, personality disorder investigation referral, stroke prevention investigation referral, and/or the like).

An example prediction-based action that can be performed using the predictive recommendation system 101 is a request for generating predictive recommendations relating to neurovascular and neurodegenerative diseases. Neurovascular and neurodegenerative diseases are characterized by progressive brain tissue loss and/or damage that is difficult to treat effectively once overtly expressed (e.g., via memory loss, diagnosis of dementia, or stroke). Signs of overt disease can be found in a brain magnetic resonance imaging (MRI) scans more than ten (10) years prior to the onset of symptoms, which provides the potential for prognosis-based referral to specialist secondary services (e.g., cognitive impairment, Alzheimer's disease, and/or neurovascular clinics). These referrals would provide the opportunity for earlier treatment that may lead to better outcomes.

In some embodiments, predictive recommendation system 101 may communicate with at least one of the external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive recommendation system 101 may include a predictive recommendation computing entity 106 and a storage subsystem 108. The predictive recommendation computing entity 106 may be configured to receive predictive recommendation requests from one or more external computing entities 102, process the predictive recommendation requests to generate predictions corresponding to the predictive recommendation requests, provide the generated predictions to the external computing entities 102, and automatically perform prediction-based actions based at least in part on the generated predictions.

The storage subsystem 108 may be configured to store input data used by the predictive recommendation computing entity 106 to perform predictive recommendations (e.g., health-related predictive recommendations) as well as model definition data used by the predictive recommendation computing entity 106 to perform various predictive recommendation tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Recommendation Computing Entity

Figure 2:
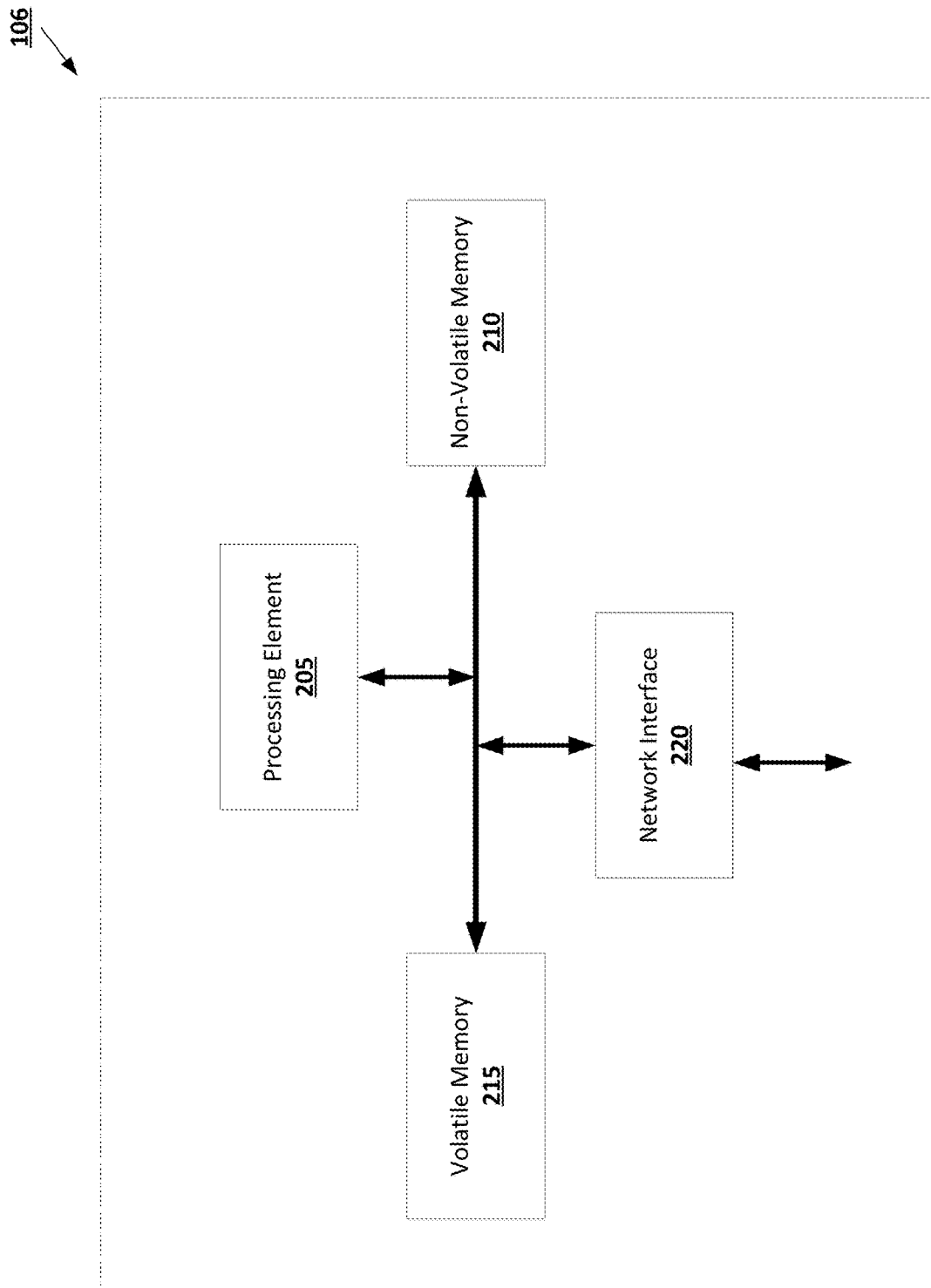
FIG. 2 provides an example predictive recommendation computing entity in accordance with some embodiments discussed herein.

FIG. 2 provides a schematic of a predictive recommendation computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive recommendation computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive recommendation computing entity 106 may include, or be in communication with, one or more processing elements 205 (also referred to as processors, processing circuitry, and/or similar terms used herein interchangeably) that communicate with other elements within the predictive recommendation computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive recommendation computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive recommendation computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive recommendation computing entity 106 with the assistance of the processing element 205 and operating system.

As indicated, in one embodiment, the predictive recommendation computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive recommendation computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive recommendation computing entity 106 may include, or be in communication with, one or more input elements, such as a keyboard input, a mouse input, a touch screen/display input, motion input, movement input, audio input, pointing device input, joystick input, keypad input, and/or the like. The predictive recommendation computing entity 106 may also include, or be in communication with, one or more output elements (not shown), such as audio output, video output, screen/display output, motion output, movement output, and/or the like.

Exemplary External Computing Entity

Figure 3:
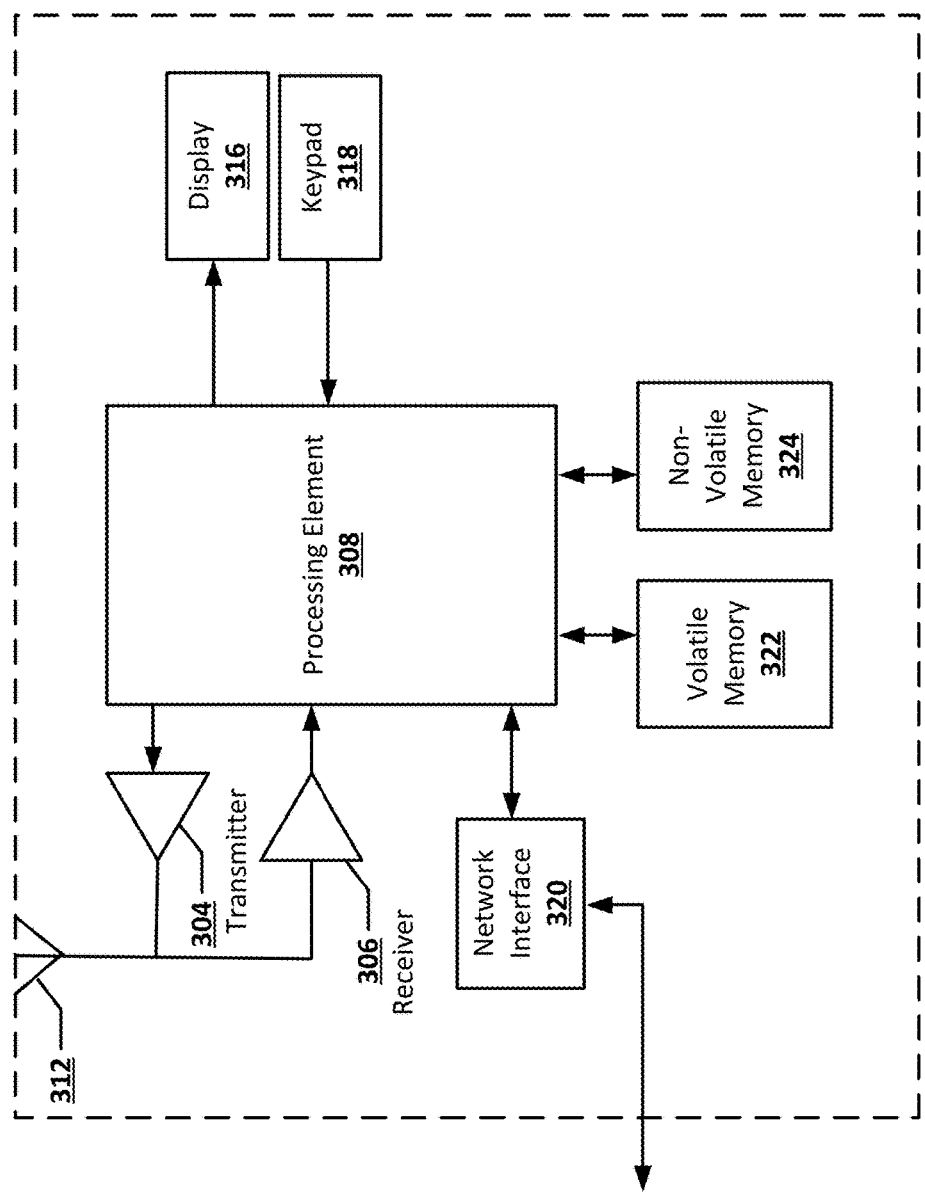
FIG. 3 provides an example external computing entity in accordance with some embodiments discussed herein.

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive recommendation computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive recommendation computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive recommendation computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive recommendation computing entity 106 and/or various other computing entities.

In another embodiment, the external computing entity 102 may include one or more components or functionality that are the same or similar to those of the predictive recommendation computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. Exemplary System Operations

As described below, various embodiments of the present invention introduce techniques that improve the training speed of magnetic resonance imaging (MRI) set processing machine learning frameworks given a constant/target predictive accuracy by introducing a MRI set processing machine learning framework architecture that comprises an image preprocessing model, an image segmentation model, a voxel integrity score generation machine learning model, an integrity score normalization model, and a region scoring model. The combination of the noted components enables the proposed MRI set processing machine learning framework to generate more accurate MRI-based predictions, which in turn increases the training speed of the proposed MRI set processing machine learning framework given a constant predictive accuracy. It is well-understood in the relevant art that there is typically a tradeoff between predictive accuracy and training speed, such that it is trivial to improve training speed by reducing predictive accuracy, and thus the real challenge is to improve training speed without sacrificing predictive accuracy through innovative model architectures. See, e.g., Sun et al., *Feature-Frequency-Adaptive On-line Training for Fast and Accurate Natural Language Processing* in 40(3) Computational Linguistic 563 at Abst. ("Typically, we need to make a tradeoff between speed and accuracy. It is trivial to improve the training speed via sacrificing accuracy or to improve the accuracy via sacrificing speed. Nevertheless, it is nontrivial to improve the training speed and the accuracy at the same time"). Accordingly, techniques that improve predictive accuracy without harming training speed, such as various techniques described herein, enable improving training speed given a constant predictive accuracy. Therefore, by improving accuracy of performing MRI-based ML predictions, various embodiments of the present invention improve the training speed of magnetic resonance imaging (MRI) set processing machine learning frameworks given a constant/target predictive accuracy.

Figure 4:
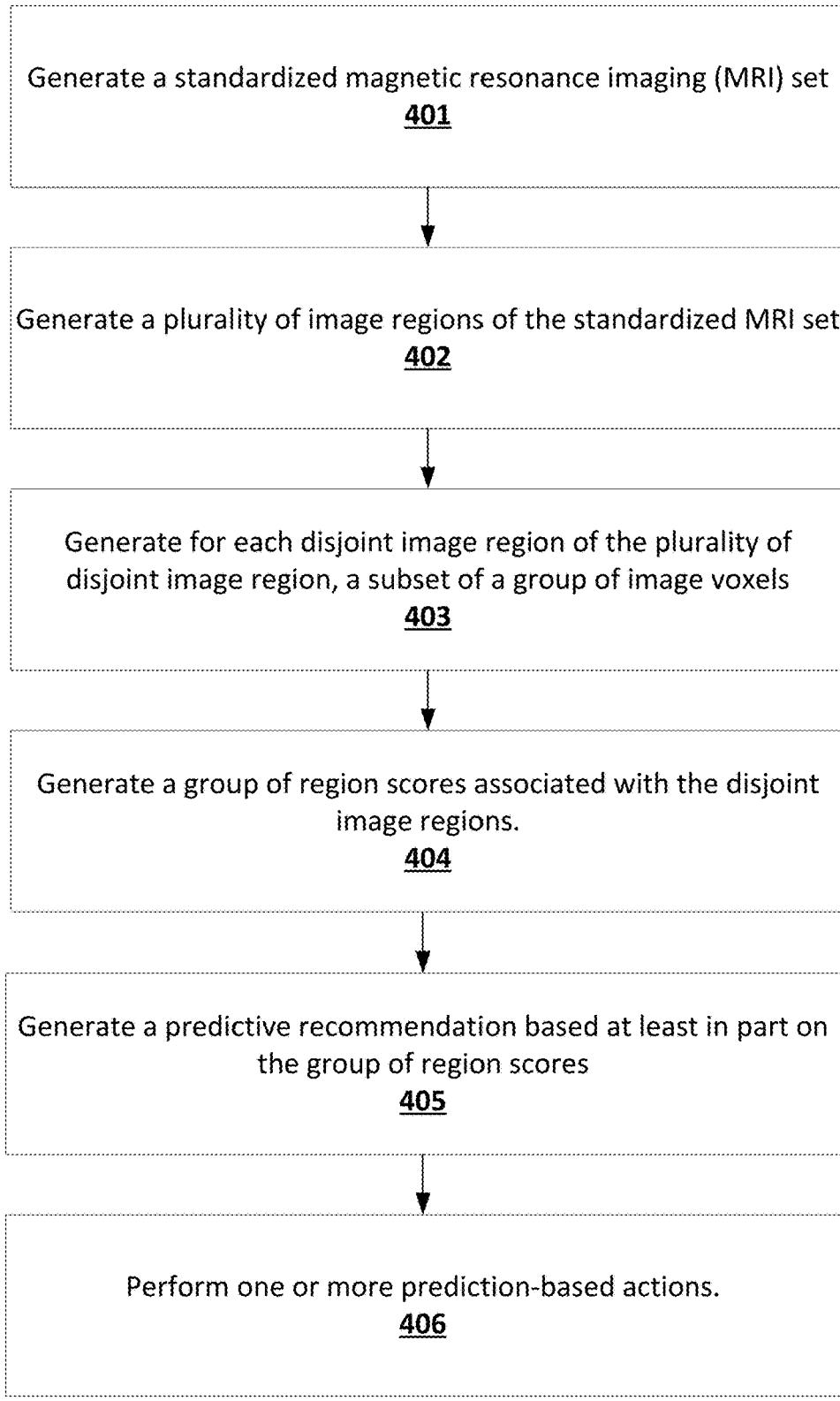
FIG. 4 is a flowchart diagram of an example process for generating predictive recommendations based at least in part on a magnetic resonance imaging (MRI) set in accordance with some embodiments discussed herein.

FIG. 4 provides a flowchart diagram of an example process for generating predictive recommendations based at least in part on a magnetic resonance imaging (MRI) set. While various embodiments of the present invention describe combining multiple techniques (e.g., techniques using preprocessing models, techniques using image segmentation models, techniques using a standardized MRI set, techniques using voxel integrity score generation machine learning model, techniques using voxel input representations of an image voxel) to generate a non-parametric integrity ranking that is in turn utilized to generate predicted recommendations for a for a patient/monitored individual associated with a common target object, a person of ordinary skill in the relevant technology will recognize that each of the disclosed techniques can be performed individually without using the other disclosed techniques. Moreover, while various embodiments of the present invention describe performing the noted multiple techniques using a singular computing entity, a person of ordinary skill in the relevant technology will recognize that each of the disclosed techniques can be performed by a separate computing entity. The process 400 will now be described with reference to the predictive recommendation computing entity 106 of the predictive recommendation system 101, as described above in relation to FIG. 1.

The process 400 that is depicted in FIG. 4 begins at step/operation 401 when the predictive recommendation computing entity 106 performs one or more image preprocessing operations on a magnetic resonance imaging (MRI) set of a common target object, where the MRI set may be characterized by one or more MRI images that are associated with the common target object having a common target object type. In some embodiments, the MRI set may be generated in accordance with a multi-sequence MRI acquisition protocol, where each sequence (e.g., T1, T2, and/or the like) corresponds to an MRI image. In some embodiments, the one or more MRI images comprise a T1-weighted MRI image, a T2-weighted MRI image, a T2*-weighted MRI image, and a Fluid Attenuated Inversion Recovery (FLAIR) MRI image. In some embodiments, the common target object may be a brain region (e.g., of a patient). Dickie et al., 2018. *The brain health index: Towards a combined measure of neurovascular and neurodegenerative structural brain injury* discloses example techniques for performing image preprocessing.

In some embodiments, the one or more image preprocessing operations comprise generating a standardized magnetic resonance imaging (MRI) set of the common target object based at least in part on the MRI set (e.g., raw MRI images) of the common target object. A standardized MRI set may describe an MRI set where the MRI images of the MRI set have been co-registered such that corresponding voxels representing the same point in a three-dimensional space with respect to the common target object are aligned. Dickie et al., 2018. *The brain health index: Towards a combined measure of neurovascular and neurodegenerative structural brain injury* discloses example techniques for co-registering MRI images. In some embodiments, the predictive recommendation computing entity 106 generates the standardized MRI set of the common target object by applying (or otherwise utilizing) an image preprocessing model to the common target object. In some embodiments, as discussed above, generating the standardized MRI set of the common target object comprise co-registering the MRI images of the MRI set, where co-registering the MRI images may comprise overlaying the MRI images such that each corresponding voxel representing the same point in a three-dimensional space of the MRI images are aligned. For example, in some embodiments, generating the standardized MRI set comprises overlaying a T1-weighted MRI image, a T2-weighted MRI image, a T2*-weighted MRI image, and a Fluid Attenuated Inversion Recovery (FLAIR) MRI image of the common target object. In some embodiments, additional preprocessing operations may be performed. An example of such preprocessing operations may comprise extracting a portion of each MRI image of the MRI set. For example, in some embodiments, the additional one or more preprocessing operations may comprise extracting a portion of each MRI image corresponding to the brain of the predictive entity (e.g., patient) associated with the MRI set (e.g., removing the skull and other extra-cranial structures). See Dickie et al., 2018. *The brain health index: Towards a combined measure of neurovascular and neurodegenerative structural brain injury*.

FIG. 5 provides an operational example 500 for a generating a standardized MRI set for a common target object. In the depicted operational example of FIG. 5, the common target object is a brain region. As shown in FIG. 5, the MRI set comprises four MRI images 500A-D of a brain region captured (e.g., at step/operation 501) utilizing a multi-sequence MRI acquisition protocol (e.g., a T1-weighted MRI image, a T2-weighted MRI image, a T2*-weighted MRI image, and a Fluid Attenuated Inversion Recovery (FLAIR) MRI image). As depicted in FIG. 5, the MRI images 500A-D are co-registered/overlaid (e.g., at step/operation 502), thus aligning corresponding voxels. Furthermore, as depicted in FIG. 5, for each MRI image, the portion corresponding to the brain is extracted by removing the skull and other cranial structures (e.g., at step/operation 503). The generated standardized MRI set comprises four overlaid MRI images 504A-D as shown in FIG. 5.

At step/operation 402, the predictive recommendation computing entity 106 generates a plurality of disjoint image regions of the standardized MRI set. In various embodiments, the predictive recommendation computing entity 106 generates the plurality of disjoint image regions utilizing an image segmentation model that is configured to process the standardized MRI set in order to generate the disjoint image regions for the standardized MRI set, where each disjoint image region may correspond to a defined region of the common target object (e.g., with respect to the common target object type of the common target object). For example, in various embodiments, the image segmentation model may be configured to receive the MRI set as input, and process the MRI set utilizing one or more of various segmentation techniques and/or based at least in part on the common target object type of the common target object, and generate as output, an MRI set with defined regions (e.g., disjoint image regions). As discussed above, in some embodiments, the common target object may be a brain region. Accordingly, in the noted example, each disjoint image region of the plurality of disjoint image regions may correspond to a defined brain segment/region (e.g., frontal lobe, temporal lobe, parietal lobe, occipital lobe, periventricular white matter, hippocampus, amygdala, and/or the like).

At step/operation 403, the predictive recommendation computing entity 106 generates for each disjoint image region of the plurality of disjoint image regions, a subset of image voxels of a group of image voxels of the standardized MRI set. A group of image voxels may describe a plurality of voxels defining the MRI set in a three-dimensional space, where each image voxel of the group of image voxels may represent a point in the three-dimensional space. In various embodiments, the predictive recommendation computing entity 106 may generate the subset of image voxels for each disjoint image region using one or more techniques and/or models. In some embodiments, the predictive recommendation computing entity 106 may generate the subset of image voxels for each disjoint image region utilizing an image segmentation model (as described above). For example, the image segmentation model may be configured to, in addition to generating disjoint image regions for the common target object, generate (or otherwise identify) the image voxels for each disjoint image region. As discussed above, in various embodiments, the group of image voxels of the standardized MRI set may comprise a plurality of image voxels for the standardized MRI set, where an image voxel may describe a three-dimensional pixel (e.g., pixel with volume) that corresponds to a point within the image space. In some embodiments, generating the group of image voxels comprises transforming each MRI image of the MRI set from a three-dimensional matrix into vectors, where each vector may be an n-dimensional vector, and each value of the plurality of values of a given vector may correspond to an image voxel value as determined based at least in part on a respective MRI image of the MRI set (described further below). In some embodiments, generating the subset of the group of image voxels for each disjoint image region may comprise identifying the image voxels of the group of image voxels that correspond to the respective disjoint image region.

At step/operation 404, the predictive recommendation computing entity 106 generates a group of region scores for the MRI set of the common target object, where each region score of the group of region scores is associated with a respective disjoint image region of the plurality of disjoint image regions of the standardized MRI set. In other words, the predictive recommendation computing entity 106 may be configured to generate for each disjoint image region, one or more region scores, where the one or more region scores for each disjoint image region collectively define the group of region scores. In various embodiments, each region score of the group of region scores is generated based at least in part on a non-parametric integrity ranking of those image voxels that are in the respective disjoint image region. In some embodiments, the group of region scores comprise, for each disjoint image region, a normality-distribution region score. Additionally and/or alternatively, in some embodiments, the group of region scores comprise, for each disjoint image region, a normality-ratio region score. In some embodiments, the group of region scores comprise, for each disjoint image region, a normality-distribution region score and/or a normality-ratio region score. In some embodiments, the step operation 404 may be performed in accordance with the process 600 that is depicted in FIG. 6, which is an example process for generating a group of region scores for a common target object.

The process 600 that is depicted in FIG. 6 begins at step/operation 601 when the predictive recommendation computing entity 106 generates a voxel integrity score for each image voxel associated with the MRI set for the common target object. The predictive recommendation computing entity 106 may utilize various techniques and/or models to generate the voxel integrity score for an image voxel (e.g., clustering, neural networks, logistic regressions, and/or the like). In some embodiments, the predictive recommendation computing entity 106 generates the voxel integrity score for each image voxel utilizing a voxel integrity score generation machine learning model and based at least in part on a voxel input representation for the image voxel. For each image voxel, the voxel input representation for the respective image voxel may comprise a n-dimensional vector (as discussed above) where n represents the number of MRI images of the MRI set, and where each value of the n-dimensional vector corresponds to an image voxel value (e.g., intensity value) for the image voxel as determined based at least in part on the respective MRI image of the MRI set. For example, in various embodiments, the voxel input representation for each image voxel of a particular image voxel may be a four-dimensional vector comprising a first value for the image voxel as determined based at least in part on the T1-weighted MRI image, a second value for the image voxel as determined based at least in part on the T2-weighted MRI image, a third value for the image voxel as determined based at least in part on the T2*-weighted MRI image, and a fourth value for the image voxel as determined based at least in part on the Fluid Attenuated Inversion Recovery (FLAIR) MRI image.

In some embodiments, the voxel integrity score generation machine learning model is configured to receive the voxel input representation for each image voxel and output a voxel integrity score for the respective image voxel. In various embodiments, the voxel integrity score generation machine learning model outputs a voxel integrity score for the respective image voxel in the range of 0 (zero) to 1 (one), where values closer to one indicate higher brain tissue integrity and values closer to zero indicate a lower brain tissue integrity. It should be understood that in some embodiments, the voxel integrity score generation machine learning model may be configured to output voxel integrity scores in a different range.

In some embodiments, to generate the voxel integrity score for each image voxel, the voxel integrity score generation machine learning model utilizes one or more clustering techniques. Examples of clustering techniques that may be used by the voxel integrity score generation machine learning model includes clustering techniques based at least in part on connectivity models (e.g., hierarchical clustering), clustering techniques based at least in part on centroid models (e.g., k-means algorithm), clustering techniques based at least in part on distribution models (e.g., using multivariate normal distributions), clustering techniques based at least in part on density models, clustering techniques based at least in part on subspace model (e.g., using bi-clustering). In some embodiments, the voxel integrity score generation machine learning model is a gaussian mixture model cluster analysis machine learning model configured to receive as input each voxel input representation for each image voxel, and output a voxel integrity score for each respective image voxel. Exemplary techniques (e.g., utilizing clustering analysis) are disclosed in Dickie et al., 2018. *The brain health index: Towards a combined measure of neurovascular and neurodegenerative structural brain injury.*

In various embodiments, the voxel integrity score generation machine learning model that is a gaussian mixture model cluster analysis machine learning model may be configured to determine the voxel integrity score for each image voxel utilizing an expectation-maximization (EM) algorithm and based at least in part on the n-dimensional vector representation (e.g., voxel input representation), where, as discussed above, each image voxel value of the n-dimensional vector representation may describe at least in part an intensity value of the image voxel as determined by each MRI image associated with the MRI set (e.g., T1-weighted MRI image, T2-weighted MRI image, T2*-weighted MRI image, and Fluid Attenuated Inversion Recovery (FLAIR) MRI image). In various embodiments, the voxel integrity score generation machine learning model that is a gaussian mixture model cluster analysis machine learning model, utilizing an expectation-maximization (EM) algorithm, determines a cluster classification probability measure for each image voxel based at least in part on each image voxel value in the input vector representation for the image voxel, where a cluster classification probability measure may describe a posterior probability that describes the likelihood that the corresponding image voxel is associated with a particular cluster classification of the plurality of cluster classifications. In some embodiments the plurality of cluster classifications may comprise a first classification that describes a normal condition and a second classification that describes an abnormal condition. In some embodiments, subsequent to determining the cluster classification probability measure for each image voxel, utilizing the expectation-maximization (EM) algorithm, the voxel integrity score generation machine learning model that is a gaussian mixture model cluster analysis machine learning model estimates one or more of a cluster means, covariance matrices, and mixing portions based at least in part on each cluster classification probability until convergence is attained, where, each cluster classification probability may describe a weight value and where convergence may be attained when the distance between each image voxel and the multi-variate cluster mean is minimized. See Dickie et al., 2018. *The brain health index: Towards a combined measure of neurovascular and neurodegenerative structural brain injury.*

Figure 7:
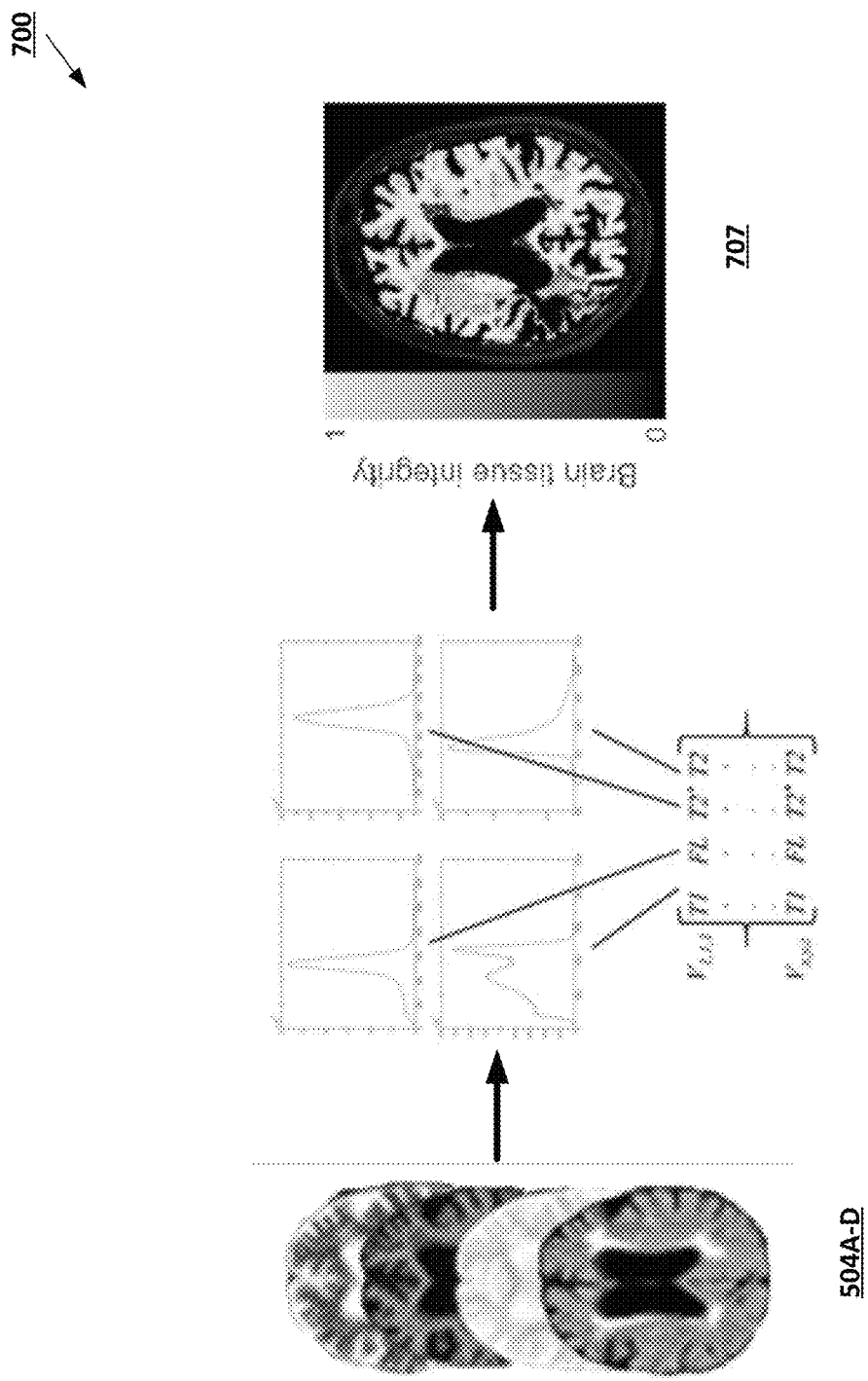
FIG. 7 provides an operational example for generating a voxel integrity score for each image voxel in accordance with some embodiments discussed herein.

FIG. 7 provides an operational example 700 for generating a voxel integrity score for each image voxel. As shown in FIG. 7, for each image voxel of the standardized MRI set (e.g., 504A-D) of a common target object that is a brain region common target object, a voxel integrity score in the range of zero to one is generated for the respective image voxel based at least in part on the voxel input representation and using a voxel integrity score generation machine learning model. As shown in FIG. 7, in some embodiments, the integrity score may be depicted on a graphical representation (e.g., color map) of the MRI set (e.g., as shown in 707).

Returning to FIG. 6, at step/operation 602, the predictive recommendation computing entity 106 generates, for each image voxel, a non-parametric integrity ranking for the image voxel based at least in part on the voxel integrity score for the image voxel. In various embodiments, the predictive recommendation computing entity 106 generates the non-parametric integrity ranking for each image voxel based at least on the voxel integrity score utilizing an integrity score normalization model, where the integrity score normalization model may be characterized by a normalization space that is defined by one or more normalization variables, and where one or more of the (e.g. each) normalization variables may be associated with the common target object. In some embodiments, examples of such normalization variables include age variable, gender variable, race variable, and/or the like. As further described below, in some embodiments, the normalization space comprises, for each historical MRI set of one or more historical MRI sets that are associated with the one or more normalized variables, a group of historical voxel integrity scores for the historical MRI set that are generated based at least in part on processing the historical MRI set to generate a historical voxel integrity score distribution comprising the historical voxel integrity scores and corresponding percentile ranks.

For example, in some embodiments, generating the non-parametric integrity ranking for each image voxel may comprise comparing the voxel integrity score for the respective image voxel to a corresponding historical voxel integrity score distribution associated with the respective image voxel of a plurality of historical voxel integrity score distributions, where each historical voxel integrity score distribution may be associated with at least one normalization variable value (e.g., age). For example, in some embodiments, the corresponding historical voxel integrity score distribution associated with a given image voxel of the common target object may be determined based at least in part on the one or more normalization variables associated with the common target object. For example, where the one or more normalization variable comprises an age variable, a given voxel integrity score of the common target object may be compared to an historical voxel integrity score distribution associated with an age value that is substantially the same as the age value associated with the common target object. As an example, given a common target object that is a brain region and given that the brain region is that of an individual that is 45 years old. In the noted example, the voxel integrity scores of the common target object may be compared to an historical voxel integrity score specific to individuals that are 45 years old. As another example, given a common target object that is a brain region common target object and given that the brain region is that of an individual that is 15 years old. In the noted example, the voxel integrity scores of the common target object may be compared to an historical voxel integrity score specific to individuals that are 15 years old. Exemplary techniques for generating historical voxel integrity score distributions are disclosed in Dickie, et al., 2015. *Use of Brain MRI Atlases to Determine Boundaries of Age-Related Pathology: The Importance of Statistical Method.*

In some embodiments, each of the historical voxel integrity score distributions of the plurality of historical voxel integrity score distributions may be characterized by a plurality of percentile ranks, where each percentile rank is associated with (e.g., corresponds to) a historical voxel integrity score of a plurality of historical voxel integrity scores determined based at least in part on one or more historical MRI sets. For example, an historical voxel integrity score distribution may comprise p percentile ranks (where p may be 3, 10, 50, and/or the like) that are each associated with an historical voxel integrity score. In some embodiments, each historical voxel integrity score may be generated based at least in part on the output of processing the one or more historical MRI sets using one or more of an image preprocessing model (such as the image preprocessing model described above), an image segmentation model (such as the image segmentation model described above), and a voxel integrity score generation machine learning model (such as the voxel integrity score generation machine learning model described above). For example, in some embodiments, each historical voxel integrity score may be generated based at least in part on the output of processing the one or more historical MRI sets using an image preprocessing model (such as the image preprocessing model described above), an image segmentation model (such as the image segmentation model described above), and a voxel integrity score generation machine learning model (such as the voxel integrity score generation machine learning model described above). In some embodiments, each historical MRI set of the one or more historical MRI sets may be associated with a historical common target object of a plurality of historical common target objects having the same common object type, and/or associated with the same normalization variable (e.g., age), and/or having a common feature (or otherwise associated with a common feature).

For example, in some embodiments, the one or more historical MRI sets may be associated with brains that were deemed normal (e.g., not associated with a neurological condition, neurodegenerative condition, neurovascular condition, and/or other brain disorder). For example, an historical voxel integrity score distribution may comprise historical voxel integrity scores of a plurality of normal historical MRI sets (e.g., normal MRI images) associated with a normal brain, where each normal historical MRI set of the plurality of normal historical MRI sets is associated with one or more normalization variables (e.g., age). For example, for a particular historical voxel integrity score distribution, each historical MRI set may be associated with patients/individuals of the same age. For example, for a first historical voxel integrity score distribution, each historical MRI set used to generate the first historical voxel integrity score distribution may be associated with individuals that are 35 years old. As another example, for a second historical voxel integrity score distribution, each historical MRI set used to generate the second historical voxel integrity score distribution may be associated with individuals that are 55 years old. In the noted examples, while each MRI set may comprise normal brain MRI images (e.g., not associated with a neurological condition, neurodegenerative condition, or a neurovascular condition), the historical voxel integrity score distribution may comprise a plurality of voxel integrity scores that span a range, given the variability in brain structure regardless of cognitive function or similarity in age.

In some embodiments, generating the non-parametric integrity ranking for each image voxel by comparing the voxel integrity score for the respective image voxel to a corresponding historical voxel integrity score distribution may comprise mapping the voxel integrity score to the corresponding historical voxel integrity score distribution and determining the percentile rank in the historical voxel integrity score distribution that corresponds to the historical voxel integrity score that is proximate to the voxel integrity score for the respective image voxel (e.g., closest in value).

Figure 8:
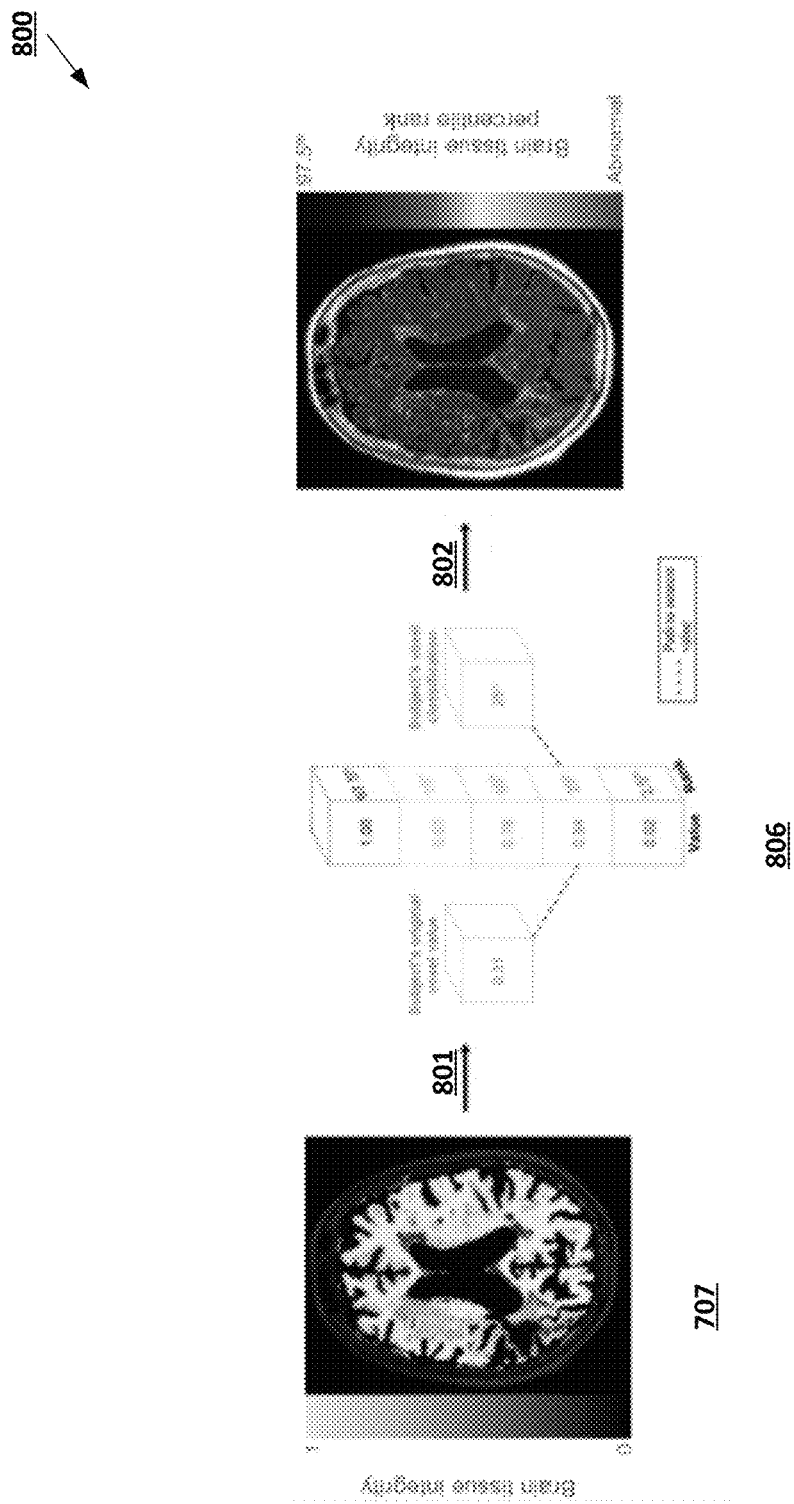
FIG. 8 provides an operational example for generating a non-parametric integrity ranking for each image voxel in accordance with some embodiments discussed herein.

FIG. 8 provides an operation example 800 for generating a non-parametric integrity ranking for each image voxel by comparing/mapping the voxel integrity score for the respective image voxel to a corresponding percentile rank in a corresponding historical voxel integrity score distribution. In the depicted operational example 800 of FIG. 8, for each image voxel, the corresponding voxel integrity score is compared with the corresponding historical voxel integrity score distribution 806 (e.g., at step/operation 801). Furthermore, as shown in FIG. 8, a non-parametric percentile ranking is generated for each image voxel (e.g., at step/operation 802) based at least in part on the percentile ranking of the historical voxel integrity score that is closest to the respective voxel integrity score for the image voxel. For example, in FIG. 8, the historical voxel integrity score that is closest to a voxel integrity score of 0.31 is 0.54, and corresponds to $25^{th}$ percentile rank. It should be noted, as discussed above, that while FIG. 8 depicts an historical voxel integrity score distribution having five percentile ranks (e.g., $2.5^{th}$, $25^{th}$, $50^{th}$, $75^{th}$, and $97.5^{th}$), an historical voxel integrity score distribution may comprise less than five percentile ranks or more than five percentile ranks.

Returning to FIG. 6, at step/operation 603, the predictive recommendation computing entity 106 generates the group of region scores based at least in part on each non-parametric integrity ranking, where each region score of the group of region scores is associated with a respective disjoint image region and is generated based at least in part on each non-parametric integrity ranking for those image voxels that are in the respective disjoint image region. Each region score for a respective disjoint image region may be determined (e.g., calculated) based at least in part on one or more of a variety of methods. For example, a particular region score may be determined based at least in part on aggregating each non-parametric integrity ranking for those image voxels that are in the respective disjoint image region, calculating a variance of non-parametric integrity rankings for those image voxels that are in the respective disjoint image region, calculating the skewness of non-parametric integrity rankings for those image voxels that are in the respective disjoint image region, and/or the like. In some embodiments, the group of region scores comprise, for each disjoint image region, a normality-distribution region score and/or a normality-ratio region score. In some embodiments, the normality-distribution region score for a disjoint image region is generated based at least in part on an average measure (e.g., average) of each non-parametric integrity ranking for those image voxels that are in the respective disjoint image region. In some embodiments, the normality-ratio region score for a disjoint image region is generated based at least in part on a ratio of image voxels that are in the disjoint image region and that are associated with non-threshold-satisfying non-parametric integrity rankings and image voxels that are in the disjoint image region and that are associated with threshold-satisfying non-parametric integrity rankings. In some embodiments, a threshold-satisfying non-parametric integrity ranking may refer to a data entity that is configured to describe a non-parametric integrity ranking with respect to an image voxel that satisfies a defined integrity ranking threshold, where a non-parametric integrity ranking that satisfies the defined integrity ranking threshold may be deemed to be associated with a normal classification. Additionally, in some embodiments, a non-threshold-satisfying non-parametric integrity ranking may refer to a data entity that is configured to describe a non-parametric integrity ranking with respect to an image voxel that fails to satisfy a defined integrity ranking threshold, where in some embodiments, a non-parametric integrity ranking that fails to satisfy the defined integrity ranking threshold may be deemed to be associated with an abnormal classification. In some embodiments, for each disjoint image region of a common target object, each image voxel in the corresponding disjoint image region may be compared to the defined integrity ranking threshold in order to determine whether the respective image voxel is associated with a threshold-satisfying non-parametric integrity ranking or a non-threshold-satisfying non-parametric integrity ranking. In some embodiments, the defined integrity ranking threshold may be the lowest percentile rank value in a historical voxel integrity score distribution.

Returning to FIG. 4, at step/operation 405, the predictive recommendation computing entity 106 generates one or more predictive recommendations based at least in part on the group of region scores. In some embodiments, the predictive recommendation computing entity 106 generates the one or more predictive recommendations utilizing a predictive recommendation model. In various embodiments, the predictive recommendation model is configured to map the group of region scores to a selected subset of a plurality of candidate predictive recommendations. In various embodiments, the predictive recommendation model is characterized by a plurality of predictive recommendation mapping rules comprising one or more normality-distribution predictive recommendation mapping rules and/or one or more normality-ratio predictive recommendation mapping rules. In some embodiments, the predictive recommendation mapping rules may be determined from radiological literature and/or determined (e.g., utilizing machine learning) from historical recommendations made by radiologists. In various embodiments, each normality-distribution predictive recommendation mapping rule is characterized by a normality-distribution region score threshold and each normality-ratio predictive recommendation mapping rule is characterized by a normality-ratio region score threshold.

Figure 9A:
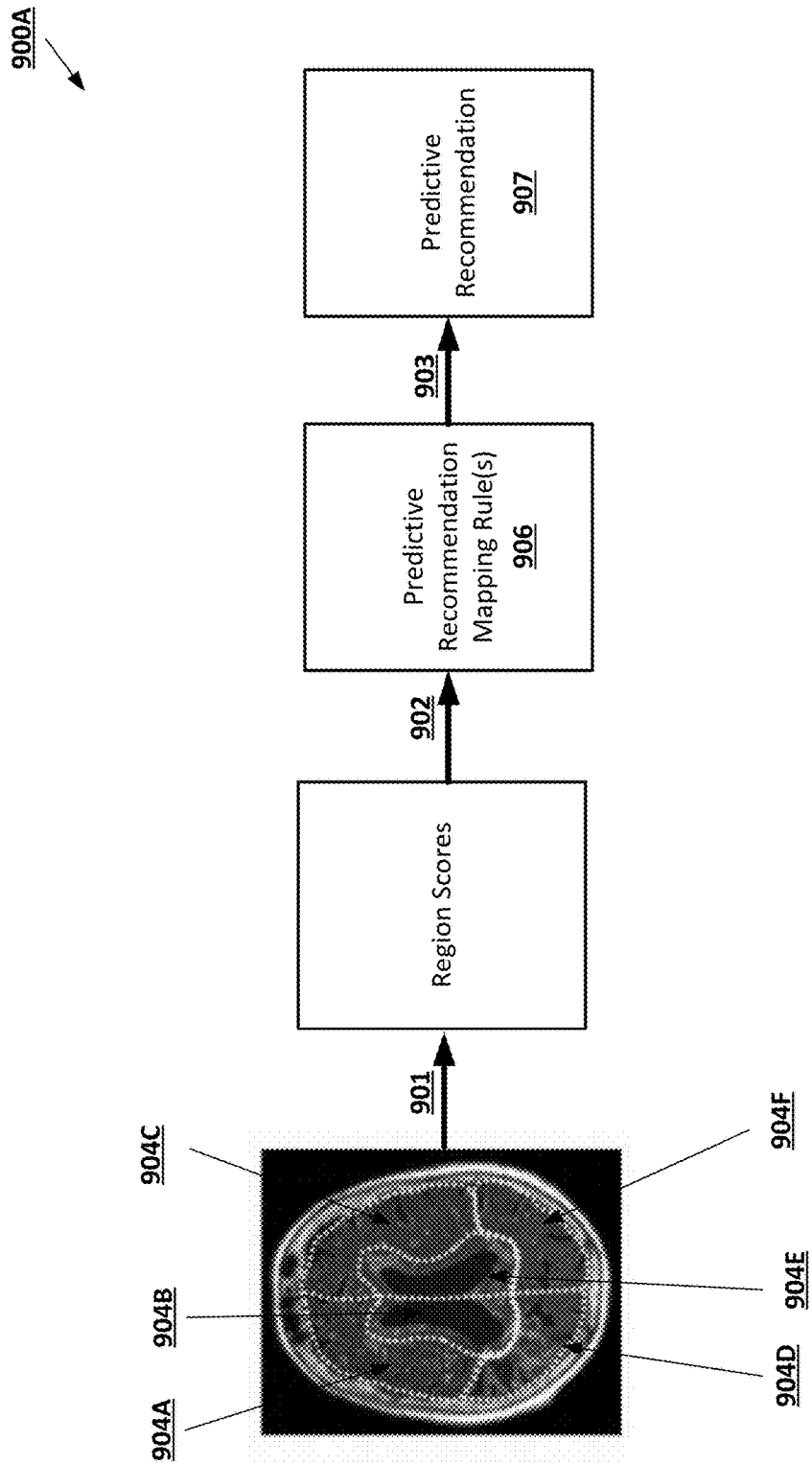

FIGS. 9A-9B provide operational examples 900A-B for predictive recommendation illustrating various predictive recommendation mapping rules. As shown in FIGS. 9A-9B, for each disjoint image region 904A-F, the region scores (e.g., normality-ratio region score and/or normality-distribution region score) may be generated, e.g., at step/operation 901. The normality-ratio region score and/or the normality-distribution region score for the particular disjoint image region may then be mapped, based at least in part on one or more predictive recommendation mapping rules (e.g., normality-distribution region score less than $25^{th}$ percentile, normality ratio region score greater than 0.35, and/or the like) 906, e.g., at step/operation 902, to a selected subset of a plurality of candidate predictive recommendations in order to generate a predictive recommendation 907 (e.g., at step/operation 903). FIG. 9B, depicts a plurality of disjoint image regions 904A-N and corresponding predictive recommendation mapping rules with the respective normality-distribution region score threshold (e.g. less than $25^{th}$ percentile, less than $2.5^{th}$ percentile, and the like) and/or normality ratio region score threshold (e.g., greater than 0.35, greater than 0.5, and the like) 906, as well as the corresponding predictive recommendations 907.

Returning to FIG. 4, at step/operation 406, the predictive recommendation computing entity 106 performs one or more prediction-based actions based at least in part on the selected subset of the plurality of candidate predictive recommendations. For example, the predictive recommendation computing entity 106 may be configured to generate one or more physician alerts and/or one or more healthcare alerts based at least in part on the selected subset of the plurality of candidate predictive recommendations. As another example, the predictive recommendation computing entity 106 may be configured to generate one or more automated physician appointments, automated medical notes, automated prescription medications, automated physician instruction, and/or the like based at least in part on the selected subset of the plurality of candidate predictive recommendations. In some embodiments, the predictive recommendation computing entity may be configured to generate user interface data for display using a display device of a computing entity (e.g., external computing entity 102). For example, in some embodiments, the predictive recommendation computing entity 106 generates user interface data for one or more recommendations (e.g., referrals) based at least in part on the selected subset of the plurality of candidate predictive recommendations.

In some embodiments, performing the prediction-based actions comprises generating user interface data for a prediction output user interface that displays predictive recommendations for a patient based on the MRI set for the patient. An operational example of such a prediction output user interface 1000 is depicted in FIG. 10. In some embodiments, performing the prediction-based actions may comprise overlaying the ranked MRI set (e.g., color map of the standardized MRI set after processing) on the MRI set (e.g., standardized MRI set prior to processing) and displaying to a medical provider (e.g., physician, and/or the like). For example, overlaying the ranked image as described above may highlight subtle insidious brain changes in a small number of image voxels that may not be perceivable by the naked eye or be washed out in the regional scores.

In some embodiments, the voxel integrity score generation machine learning model utilize operations that may, in at least some embodiments, reduce or eliminate the need for computationally expensive training operations in order to generate the noted voxel integrity score generation machine learning model. By reducing or eliminating the noted training operations, various embodiments of the present invention: (i) reduce or eliminate the computational operations needed for training and thus improves the computational efficiency of performing predictive recommendations using MRI sets, (ii) reduce or eliminate the need for storage resources to train/generate voxel integrity score generation machine learning model and thus improves storage efficiency of performing predictive recommendations, and (iii) reduces or eliminates the need for transmitting extensive training data needed to generate voxel integrity score generation machine learning model and thus improves transmission/network efficiency of performing predictive recommendations using MRI sets. Via the noted advantages, various embodiments of the present invention make substantial technical contributions to the fields of predictive recommendations in particular and healthcare-related predictive recommendation in general.

In some embodiments, performing the prediction-based actions includes performing operational load balancing for the post-prediction systems that perform post-prediction operations (e.g., automated specialist appointment scheduling operations) based on MRI-based predictions. For example, in some embodiments, a predictive recommendation computing entity determines D classifications for D MRI image sets based at least in part whether D MRI image sets based on whether the selected region subset for each MRI image set as generated by the predictive recommendation model comprises a target region (e.g., a target brain region). Then, the count of D MRI image sets that are associated with an affirmative classification, along with a resource utilization ratio for each MRI image set, can be used to predict a predicted number of computing entities needed to perform post-prediction processing operations with respect to the D MRI image sets. For example, in some embodiments, the number of computing entities needed to perform post-prediction processing operations (e.g., automated specialist scheduling operations) with respect to D MRI image sets can be determined based at least in part on the output of the equation:

$$R = \text{ceil}\left(\sum\nolimits_{k}^{k=K} ur_k\right),$$

where R is the predicted number of computing entities needed to perform post-prediction processing operations with respect to the D MRI image sets, ceil(.) is a ceiling function that returns the closest integer that is greater than or equal to the value provided as the input parameter of the ceiling function, k is an index variable that iterates over K MRI image sets among the D MRI image sets that are associated with affirmative classifications, and $ur_k$ is the estimated resource utilization ratio for a kth MRI image set that may be determined based at least in part on a patient history complexity of a patient associated with the MRI image set. In some embodiments, once R is generated, a predictive recommendation computing entity can use R to perform operational load balancing for a server system that is configured to perform post-prediction processing operations with respect to D MRI image sets. This may be done by allocating computing entities to the post-prediction processing operations if the number of currently-allocated computing entities is below R, and deallocating currently-allocated computing entities if the number of currently-allocated computing entities is above R.

Accordingly, as described above, various embodiments of the present invention introduce techniques that improve the training speed of magnetic resonance imaging (MRI) set processing machine learning frameworks given a constant/target predictive accuracy by introducing a MRI set processing machine learning framework architecture that comprises an image preprocessing model, an image segmentation model, a voxel integrity score generation machine learning model, an integrity score normalization model, and a region scoring model. The combination of the noted components enables the proposed MRI set processing machine learning framework to generate more accurate MRI-based predictions, which in turn increases the training speed of the proposed MRI set processing machine learning framework given a constant predictive accuracy. It is well-understood in the relevant art that there is typically a tradeoff between predictive accuracy and training speed, such that it is trivial to improve training speed by reducing predictive accuracy, and thus the real challenge is to improve training speed without sacrificing predictive accuracy through innovative model architectures. See, e.g., Sun et al., *Feature-Frequency—Adaptive On-line Training for Fast and Accurate Natural Language Processing* in 40(3) Computational Linguistic 563 at Abst. ("Typically, we need to make a tradeoff between speed and accuracy. It is trivial to improve the training speed via sacrificing accuracy or to improve the accuracy via sacrificing speed. Nevertheless, it is nontrivial to improve the training speed and the accuracy at the same time"). Accordingly, techniques that improve predictive accuracy without harming training speed, such as various techniques described herein, enable improving training speed given a constant predictive accuracy. Therefore, by improving accuracy of performing MRI-based ML predictions, various embodiments of the present invention improve the training speed of magnetic resonance imaging (MRI) set processing machine learning frameworks given a constant/target predictive accuracy.

VI. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for generating one or more predictive recommendations based at least in part on a magnetic resonance imaging (MRI) set characterized by one or more MRI images that are associated with a common target object having a common target object type, the computer-implemented method comprising:
generating, using one or more processors and an image preprocessing model for the common target object type, and based at least in part on the MRI set, a standardized MRI set;
generating, using the one or more processors and an image segmentation model, and based at least in part on the standardized MRI set: (i) a plurality of disjoint image regions of the standardized MRI set, and (ii) for each disjoint image region, a subset of a group of image voxels of the standardized MRI set;
for each image voxel, using the one or more processors:
generating, using a voxel integrity score generation machine learning model, and based at least in part on a voxel input representation for the image voxel, a voxel integrity score for the image voxel, and
generating, using an integrity score normalization model characterized by a normalization space that is defined by one or more normalization variables associated with the common target object, and based at least in part on the voxel integrity score for the image voxel, a non-parametric integrity ranking for the image voxel;
generating, using the one or more processors, a group of region scores based at least in part on each non-parametric integrity ranking, wherein:
each region score is associated with a respective disjoint image region and is generated based at least in part on each non-parametric integrity ranking for those image voxels that are in the respective disjoint image region, and
the group of region scores comprise, for each disjoint image region: (i) a normality-distribution region score that is generated based at least in part on an average measure of each non-parametric integrity ranking for those image voxels that are in the respective disjoint image region, and (ii) a normality-ratio region score that is generated based at least in part on a ratio of those image voxels that are in the disjoint image region and that are associated with non-threshold-satisfying non-parametric integrity rankings and those image voxels that are in the disjoint image region and that are associated with threshold-satisfying non-parametric integrity rankings;
generating, using the one or more processors and a predictive recommendation model and based at least in part on the group of region scores, the one or more predictive recommendations, wherein:
the predictive recommendation model is configured to map the group of region scores to a selected subset of a plurality of candidate predictive recommendations, the predictive recommendation model is characterized by a plurality of predictive recommendation mapping rules comprising one or more normality-distribution predictive recommendation mapping rules and one or more normality-ratio predictive recommendation mapping rules, each normality-distribution predictive recommendation mapping rule is characterized by a normality-distribution region score threshold, and each normality-ratio predictive recommendation mapping rule is characterized by a normality-ratio region score threshold; and performing, using the one or more processors, one or more prediction-based actions based at least in part on the selected subset.

2. The computer-implemented method of claim 1, wherein the common target object is a brain region, and the plurality of disjoint image regions comprise a plurality of defined brain regions.

3. The computer-implemented method of claim 1, wherein the one or more MRI images comprise a T1-weighted MRI image, a T2-weighted MRI image, a T2*-weighted MRI image, and a Fluid Attenuated Inversion Recovery (FLAIR) MRI image.

4. The computer-implemented method of claim 3, wherein each voxel input representation for a particular image voxel is a four-dimensional vector comprising a first value for the image voxel as determined based at least in part on the T1-weighted MRI image, a second value for the image voxel as determined based at least in part on the T2-weighted MRI image, a third value for the image voxel as determined based at least in part on the T2*-weighted MRI image, and a fourth value for the image voxel as determined based at least in part on the Fluid Attenuated Inversion Recovery (FLAIR) MRI image.

5. The computer-implemented method of claim 1, wherein the voxel integrity score generation machine learning model is a Gaussian mixture model cluster analysis machine learning model.

6. The computer-implemented method of claim 1, wherein the one or more normalization variables comprise an age variable.

7. The computer-implemented method of claim 1, wherein the normalization space comprises, for each historical MRI set of one or more historical MRI sets that are associated with the one or more normalization variables, a group of historical voxel integrity scores for the historical MRI set that are generated based at least in part on output of processing the historical MRI set using one or more of the image preprocessing model, the image segmentation model, and the voxel integrity score generation machine learning model.

8. An apparatus for generating one or more predictive recommendations based at least in part on a magnetic resonance imaging (MRI) set characterized by one or more MRI images that are associated with a common target object having a common target object type, the apparatus comprising at least one processor and at least one memory including program code, the at least one memory and the program code configured to, with the processor, cause the apparatus to at least:

generate, using an image preprocessing model for the common target object type, and based at least in part on the MRI set, a standardized MRI set;

generate, using an image segmentation model, and based at least in part on the standardized MRI set: (i) a plurality of disjoint image regions of the standardized MRI set, and (ii) for each disjoint image region, a subset of a group of image voxels of the standardized MRI set;

for each image voxel:
generate, using a voxel integrity score generation machine learning model, and based at least in part on a voxel input representation for the image voxel, a voxel integrity score for the image voxel, and generate, using an integrity score normalization model characterized by a normalization space that is defined by one or more normalization variables associated with the common target object, and based at least in part on the voxel integrity score for the image voxel, a non-parametric integrity ranking for the image voxel;

generate a group of region scores based at least in part on each non-parametric integrity ranking, wherein:
each region score is associated with a respective disjoint image region and is generated based at least in part on each non-parametric integrity ranking for those image voxels that are in the respective disjoint image region, and the group of region scores comprise, for each disjoint image region: (i) a normality-distribution region score that is generated based at least in part on an average measure of each non-parametric integrity ranking for those image voxels that are in the respective disjoint image region, and (ii) a normality-ratio region score that is generated based at least in part on a ratio of those image voxels that are in the disjoint image region and that are associated with non-threshold-satisfying non-parametric integrity rankings and those image voxels that are in the disjoint image region and that are associated with threshold-satisfying non-parametric integrity rankings;

generate, using a predictive recommendation model and based at least in part on the group of region scores, the one or more predictive recommendations, wherein:
the predictive recommendation model is configured to map the group of region scores to a selected subset of a plurality of candidate predictive recommendations, the predictive recommendation model is characterized by a plurality of predictive recommendation mapping rules comprising one or more normality-distribution predictive recommendation mapping rules and one or more normality-ratio predictive recommendation mapping rules, each normality-distribution predictive recommendation mapping rule is characterized by a normality-distribution region score threshold, and each normality-ratio predictive recommendation mapping rule is characterized by a normality-ratio region score threshold; and perform one or more prediction-based actions based at least in part on the selected subset.

9. The apparatus of claim 8, wherein the common target object is a brain region, and the plurality of disjoint image regions comprise a plurality of defined brain regions.

10. The apparatus of claim 8, wherein the one or more MRI images comprise a T1-weighted MRI image, a T2-weighted MRI image, a T2*-weighted MRI image, and a Fluid Attenuated Inversion Recovery (FLAIR) MRI image.

11. The apparatus of claim 10, wherein each voxel input representation for a particular image voxel is a four-dimensional vector comprising a first value for the image voxel as determined based at least in part on the T1-weighted MRI image, a second value for the image voxel as determined based at least in part on the T2-weighted MRI image, a third value for the image voxel as determined based at least in part on the T2*-weighted MRI image, and a fourth value for the image voxel as determined based at least in part on the Fluid Attenuated Inversion Recovery (FLAIR) MRI image.

12. The apparatus of claim 8, wherein the voxel integrity score generation machine learning model is a Gaussian mixture model cluster analysis machine learning model.

13. The apparatus of claim 8, wherein the one or more normalization variables comprise an age variable.

14. The apparatus of claim 8, wherein the normalization space comprises, for each historical MRI set of one or more historical MRI sets that are associated with the one or more normalization variables, a group of historical voxel integrity scores for the historical MRI set that are generated based at least in part on output of processing the historical MRI set using one or more of the image preprocessing model, the image segmentation model, and the voxel integrity score generation machine learning model.

15. A computer program product for generating one or more predictive recommendations based at least in part on a magnetic resonance imaging (MRI) acquisition protocol characterized by one or more MRI images that are associated with a common target object having a common target object type, the computer program product comprising at least one non-transitory computer-readable storage medium having computer-readable program code portions stored therein, the computer-readable program code portions configured to:
  generate, using an image preprocessing model for the common target object type, and based at least in part on the MRI set, a standardized MRI set;
  generate, using an image segmentation model, and based at least in part on the standardized MRI set: (i) a plurality of disjoint image regions of the standardized MRI set, and (ii) for each disjoint image region, a subset of a group of image voxels of the standardized MRI set;
  for each image voxel:
    generate, using a voxel integrity score generation machine learning model, and based at least in part on a voxel input representation for the image voxel, a voxel integrity score for the image voxel, and
    generate, using an integrity score normalization model characterized by a normalization space that is defined by one or more normalization variables associated with the common target object, and based at least in part on the voxel integrity score for the image voxel, a non-parametric integrity ranking for the image voxel;
  generate a group of region scores based at least in part on each non-parametric integrity ranking, wherein:
    each region score is associated with a respective disjoint image region and is generated based at least in part on each non-parametric integrity ranking for those image voxels that are in the respective disjoint image region, and
    the group of region scores comprise, for each disjoint image region: (i) a normality-distribution region score that is generated based at least in part on an average measure of each non-parametric integrity ranking for those image voxels that are in the respective disjoint image region, and (ii) a normality-ratio region score that is generated based at least in part on a ratio of those image voxels that are in the disjoint image region and that are associated with non-threshold-satisfying non-parametric integrity rankings and those image voxels that are in the disjoint image region and that are associated with threshold-satisfying non-parametric integrity rankings;
  generate, using a predictive recommendation model and based at least in part on the group of region scores, the one or more predictive recommendations, wherein:
    the predictive recommendation model is configured to map the group of region scores to a selected subset of a plurality of candidate predictive recommendations,
    the predictive recommendation model is characterized by a plurality of predictive recommendation mapping rules comprising one or more normality-distribution predictive recommendation mapping rules and one or more normality-ratio predictive recommendation mapping rules,
    each normality-distribution predictive recommendation mapping rule is characterized by a normality-distribution region score threshold, and
    each normality-ratio predictive recommendation mapping rule is characterized by a normality-ratio region score threshold; and
  perform one or more prediction-based actions based at least in part on the selected subset.

16. The computer program product of claim 15, wherein the common target object is a brain region, and the plurality of disjoint image regions comprise a plurality of defined brain regions.

17. The computer program product of claim 15, wherein the one or more MRI images comprise a T1-weighted MRI image, a T2-weighted MRI image, a T2*-weighted MRI image, and a Fluid Attenuated Inversion Recovery (FLAIR) MRI image.

18. The computer program product of claim 17, wherein each voxel input representation for a particular image voxel is a four-dimensional vector comprising a first value for the image voxel as determined based at least in part on the T1-weighted MRI image, a second value for the image voxel as determined based at least in part on the T2-weighted MRI image, a third value for the image voxel as determined based at least in part on the T2*-weighted MRI image, and a fourth value for the image voxel as determined based at least in part on the Fluid Attenuated Inversion Recovery (FLAIR) MRI image.

19. The computer program product of claim 15, wherein the voxel integrity score generation machine learning model is a Gaussian mixture model cluster analysis machine learning model.

20. The computer program product of claim 15, wherein the one or more normalization variables comprise an age variable.

* * * * *

UNITED STATES PATENT AND TRADEMARK OFFICE
CERTIFICATE OF CORRECTION

PATENT NO. : 12,150,789 B2
APPLICATION NO. : 17/805366
DATED : November 26, 2024
INVENTOR(S) : David Alexander Dickie It is certified that error appears in the above-identified patent and that said Letters Patent is hereby corrected as shown below:

In the Claims

In Column 32, Line 35, Claim 8, delete "rankings;" and insert -- rankings, --, therefor.

Signed and Sealed this
Eleventh Day of February, 2025

Coke Morgan Stewart
*Acting Director of the United States Patent and Trademark Office*